US011142692B2

United States Patent
Zhang et al.

(10) Patent No.: US 11,142,692 B2
(45) Date of Patent: Oct. 12, 2021

(54) CAPPED CO-DOPED CORE/SHELL NANOCRYSTALS FOR VISIBLE LIGHT EMISSION

(71) Applicant: The Regents of the University of California, Oakland, CA (US)

(72) Inventors: Jin Z. Zhang, Saratoga, CA (US); Jason K. Cooper, Emeryville, CA (US); Sheraz Gul, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 479 days.

(21) Appl. No.: 15/747,723

(22) PCT Filed: Jul. 27, 2016

(86) PCT No.: PCT/US2016/044298
§ 371 (c)(1),
(2) Date: Jan. 25, 2018

(87) PCT Pub. No.: WO2017/019789
PCT Pub. Date: Feb. 2, 2017

(65) Prior Publication Data
US 2018/0216003 A1  Aug. 2, 2018

Related U.S. Application Data

(60) Provisional application No. 62/198,003, filed on Jul. 28, 2015.

(51) Int. Cl.
*C09K 11/88* (2006.01)
*C09K 11/02* (2006.01)
(Continued)

(52) U.S. Cl.
CPC ............ *C09K 11/883* (2013.01); *B82Y 20/00* (2013.01); *C07C 323/60* (2013.01); *C09K 11/02* (2013.01);
(Continued)

(58) Field of Classification Search
CPC ........ C09K 11/88; C09K 11/02; C07C 323/60
(Continued)

(56) References Cited

U.S. PATENT DOCUMENTS 7,544,398 B1 * 6/2009 Chang ..................... C23C 16/40
117/108
7,687,800 B1 * 3/2010 Kar ......................... B82Y 30/00
257/14
(Continued)

FOREIGN PATENT DOCUMENTS

CN  103911155 A  7/2014
WO  2017019789 A1  2/2017

OTHER PUBLICATIONS

Zhang, Y. et al, Journal of Physical Chemistry B 2004, 108, 17805-17811.*
(Continued)

*Primary Examiner* — Arlen Soderquist
(74) *Attorney, Agent, or Firm* — Nixon Peabody LLP

(57) ABSTRACT

In various embodiments the present disclosure provides a core/shell nanocrystal comprising a core and a shell formed on the core, wherein the core/shell nanocrystal is co-doped with at least one metal dopant and at least one trivalent cation. In some embodiments, the trivalent cation is a Group 13 element. Methods of making and using the core/shell nanocrystal are also described.

24 Claims, 20 Drawing Sheets

(51) Int. Cl.
| | |
|---|---|
| *C07C 323/60* | (2006.01) |
| *B82Y 20/00* | (2011.01) |
| *C09K 11/62* | (2006.01) |
| *C09K 11/58* | (2006.01) |
| *C09K 11/64* | (2006.01) |
| *B82Y 5/00* | (2011.01) |
| *B82Y 15/00* | (2011.01) |
| *B82Y 40/00* | (2011.01) |

(52) U.S. Cl.
CPC .......... *C09K 11/025* (2013.01); *C09K 11/584* (2013.01); *C09K 11/623* (2013.01); *C09K 11/642* (2013.01); *B82Y 5/00* (2013.01); *B82Y 15/00* (2013.01); *B82Y 40/00* (2013.01); *Y10S 977/774* (2013.01); *Y10S 977/824* (2013.01); *Y10S 977/892* (2013.01); *Y10S 977/896* (2013.01); *Y10S 977/92* (2013.01); *Y10S 977/948* (2013.01); *Y10S 977/95* (2013.01); *Y10S 977/954* (2013.01)

(58) Field of Classification Search
USPC .......................................................... 436/164
See application file for complete search history.

(56) References Cited

U.S. PATENT DOCUMENTS

| | | | |
|---|---|---|---|
| 8,410,455 B2 | 4/2013 | Cao et al. | |
| 2005/0129947 A1* | 6/2005 | Peng | C09K 11/7492 428/403 |
| 2007/0264719 A1* | 11/2007 | Santra | G01N 21/648 436/57 |
| 2008/0160306 A1* | 7/2008 | Mushtaq | C09K 11/70 428/402 |
| 2008/0202383 A1* | 8/2008 | Shi | C01B 19/002 106/286.6 |
| 2008/0220593 A1* | 9/2008 | Pickett | C09K 11/025 438/478 |
| 2009/0218550 A1* | 9/2009 | Koyakutty | C09K 11/642 252/512 |
| 2009/0230382 A1* | 9/2009 | Banin | C09K 11/02 257/14 |
| 2010/0055462 A1* | 3/2010 | Cao | C09K 11/574 428/403 |
| 2010/0062154 A1* | 3/2010 | Shin | C09C 1/10 427/214 |
| 2011/0037029 A1* | 2/2011 | Liu | B82Y 30/00 252/500 |
| 2011/0062430 A1* | 3/2011 | van Veggel | B82Y 30/00 257/40 |
| 2011/0241229 A1* | 10/2011 | Naasani | C09C 1/10 257/793 |
| 2012/0104325 A1* | 5/2012 | Talapin | B82Y 30/00 252/502 |
| 2012/0175588 A1* | 7/2012 | Qiao | C09K 11/883 257/13 |
| 2012/0267234 A1* | 10/2012 | Reece | B01J 19/127 204/157.5 |
| 2013/0082216 A1* | 4/2013 | Koyakutty | H01L 33/285 252/512 |
| 2013/0134366 A1* | 5/2013 | Battaglia | C09K 11/025 252/519.4 |
| 2013/0204025 A1* | 8/2013 | Buso | C07F 3/003 556/130 |
| 2013/0299745 A1* | 11/2013 | Mattoussi | C09K 11/025 252/301.36 |
| 2014/0252316 A1* | 9/2014 | Yan | B82Y 30/00 257/24 |
| 2014/0346442 A1* | 11/2014 | Nag | H01L 29/0665 257/29 |
| 2014/0369024 A1* | 12/2014 | Xu | C08F 2/44 362/84 |
| 2015/0111303 A1* | 4/2015 | Kim | G01N 33/1826 436/110 |
| 2015/0147818 A1* | 5/2015 | Kim | B82Y 15/00 436/110 |
| 2015/0380665 A1* | 12/2015 | Kumar | C08K 9/02 136/263 |
| 2016/0308107 A1* | 10/2016 | Talapin | B82Y 30/00 |
| 2016/0380140 A1* | 12/2016 | McDaniel | C09K 11/025 136/247 |
| 2017/0162764 A1* | 6/2017 | Kan | C09K 11/703 |

OTHER PUBLICATIONS

Viswanatha, R. et al, Nano Letters 2011, 11, 4753-4758.*
Brovelli, S. et al, Nano Letters 2012, 12, 4372-4379.*
Shiohara, A. et al, Journal of Photochemistry and Photobiology C: Photochemistry Reviews 2014, 21, 2-25.*
Marshall, A. R. et al, Journal of Physical Chemistry Letters 2015, 6, 2892-2899.*
Liu, W. et al, Journal of the American Chemical Society 2008, 130, 1274-1284 and 21 pages of Supporting Information.*
Xing, G. et al, Optics Express 2008, 16, 5715-5720.*
Susumu, K. et al, Nature Protocols 2009, 4, 424-436.*
Li, L. et al, Chemistry of Materials 2009, 21, 2422-2429.*
Xie, R. et al, Journal of the American Chemical Society 2009, 131, 10645-10651 and 4 pages of Supporting Information.*
Bailon-Ruiz, S. J. et al, Materials Research Society Symposium Proceedings 2010, 1207, 1207-N10-61, 6 pages.*
Susumu, K. et al, Journal of the American Chemical Society 2011, 133, 9480-9496 and 23 pages of Supporting Information.*
Geszke-Moritz, M. et al, Journal of Luminescence 2012, 132, 987-991.*
Guo, W. et al, Theranostics 2013, vol. 3, 99-108 and 6 pages of Supporting Information.*
Wang, L. et al, Applied Surface Science 2012, 280, 673-678.*
Zeng, R. et al, CrystEngComm 2014, 16, 3414-3423.*
Chen, C. et al, Advanced Materials 2014, 26, 6313-6317.*
Guo, W. et al, Nano Research 2014, 7, 1581-1591.*
Talapin, D. V. et al, Colloids and Surfaces A: Physicochemical and Engineering Aspects 2002, 202, 145-154.*
Manzoor, K. et al, Solid State Communications 2004, 129, 469-473.*
Hiramatsu, H. et al, Chemistry of Materials 2004, 16, 2509-2511.*
Gao, X. et al, Nature Biotechnology 2004, 22, 969-976.*
Uyeda, H. T. et al, Journal of the American Chemical Society 2005, 127, 3870-3878.*
Zimmer, J. P. et al, Journal of the American Chemical Society 2006, 128, 2526-2527.*
Manzoor, K. et al, Journal of Nanoscience and Nanotechnology 2007, 7, 463-473.*
Bullen, C. et al, Langmuir 2006, 22, 3007-3013.*
Reiss, P. et al, Small 2009, 5, 154-168.*
Xie, R. et al, Journal of the American Chemical Society 2009, 131, 5691-5697.*
Pan, D. et al, Chemical Communications 2009, 4221-4223.*
Jin, H. et al, Chemical Communications 2011, 47, 1758-1760.*
Zhang, W. et al, Inorganic Chemistry 2011, 50, 4065-4072.*
Sarkar, S. et al, Angewandte Chemie 2011, 123, 6189-6193.*
Xu, S. et al, Nanotechnology 2011, 22, paper 275605, 7 pages.*
Zhang, J. et al, Chemistry of Materials 2011, 23, 3357-3361.*
Tan, Z. et al, Advanced Materials 2011, 23, 3553-3558.*
Li, S. et al, Inorganic Chemistry 2011, 50, 11958-11964.*
Akhavan, V. A. et al, Journal of Solid State Chemistry 2012, 189, 2-12.*
Greco, T. et al, SPIE 2012, 8424, paper 842439, 9 pages.*
Niu, J. Z. et al, Advanced Materials Research 2012, 549, 12-16.*
Hardzei, M. et al, Journal of Luminescence 2012, 132, 425-428.*
Zhong, H. et al, Journal of Physical Chemistry Letters 2012, 3, 3167-3175.*
Pan, H.-J. et al, Materials Express 2012, 2, 224-232.*
Song, W.-S. et al, Journal of Materials Chemistry 2012, 22, paper 21901, 8 pages with 8 pages of supplementary material.*

(56) References Cited

OTHER PUBLICATIONS

Pan, Y. et al, Journal of Materials Chemistry 2012, 22, paper23593, 9 pages.*
Mandal, G. et al, Chemical Communications 2013, 49, 624-626.*
Maity, A. R. et al, Nanoscale 2013, 5, 5506-5513.*
Kim, S. et al, ACS Nano 2013, 7, 4756-4763.*
Xiong, W.-W. et al, ACS Applied Materials & Interfaces 2013, 5, 8210-8216.*
Zhang,, W. et al, Chemistry of Materials 2014, 26, 1204-1212.*
Leng, Z. et al, Materials Letters 2014, 119, 100-103.*
Saikia, K. et al, Materials Research Express 2014, 1, paper 015014, 11 pages with 3 pages of supplementary Information.*
Wang, M. et al, RSC Advances 2014, 4, 25183-25188.*
Song, B. et al, Bulletin of the Korean Chemical Society 2014, 35, 3601-3608.*
Jiang, T. et al, Journal of Materials Chemistry B 2015, 3, 2402-2410.*
Kim, S, et al, Small 2011, 7, 70-73.*
International Search Report and Written Opinion for PCT/US2016/044298 dated Dec. 12, 2016, 10 pages.
Cooper et al., Tunable Photoluminescent Core/Shell Cu+-Doped ZnSe/ZnS Quantum Dots Codoped with Al3+, GA3+, or In3+, ACS, Applied Materials & Interfaces, 2015, vol. 7(18), pp. 10055-10066.
Pandey et al., Long-lived photoinduced magnetization in copper-doped ZnSe-CdSe core-shell nanocrystals, Nature Nanotechnology, 2012, vol. 7, pp. 792-797.
Giannozzi et al., Quantum Espresso: a modular and open-source software project for quantum simulations of materials. Journal of Physics: Condensed Matter, 2009, vol. 21, 395502, pp. 1-19.
Newville et al., IFEFFIT: interactive XAFS analysis and FEFF fitting. Journal of Synchrotron Radiation, 2001, vol. 8, pp. 322-324.
Gul et al., Effect of Al3+ Co-doping on the Dopant Local Structure, Optical Properties, and Exciton Dynamics in Cu+-Doped ZnSe Nanocrystals. ACS Nano, 2013, vol. 7, pp. 8680-8692.
Gul et al., Effect of Al3+ Co-doping on the Dopant Local Structure, Optical Properties, and Exciton Dynamics in Cu+-Doped ZnSe Nanocrystals. ACS Nano, 2013, vol. 7, pp. 8680-8692. Supporting Information.
Liu et al., Tuning emission and Stokes shift of CdS quantum dots via copper and indium co-doping. RSC Advances, 2015, vol. 5, pp. 628-634.
Gul et al., Synthesis, Optical and Structural Properties, and Charge Carrier Dynamics of Cu-Doped ZnSe Nanocrystals. Journal of Physical Chemistry C, 2011, vol. 115, pp. 20864-20875.
Gul et al., Synthesis, Optical and Structural Properties, and Charge Carrier Dynamics of Cu-Doped ZnSe Nanocrystals. Journal of Physical Chemistry C, 2011, vol. 115, pp. 20864-20875. Supporting Information.
Zhang et al., Rational Codoping as a Strategy to Improve Optical Properties of Doped Seimiconductor Quantum Dots, Journal of Physical Chemistry Letters, 2014, vol. 5, 3694-3700.
Ravel et al., Athena, Artemis, Hephaestus: data analysis for X-ray absorption spectroscopy using IFEFFIT. Journal of Synchrotron Radiation, 2005, vol. 12, pp. 537-541.
Zabinsky et al., Multiple-scattering calculations of x-ray-absorption spectra. Physical Review B 1995, vol. 52, pp. 2995-3009.
Ramanathan S. et al., Fluorescence spectroscopy of electrochemically self-assembled ZnSe and Mn:ZnSe nanowires. Nanotechnology 2008, vol. 19, 195601, pp. 1-6.
Pawlikowski, J. M. Absorptivity and photoluminescence of compensated ZnSe:Ga. Solid State Commun. 1985, vol. 55, pp. 31-33.
International Preliminary Report on Patentability for PCT/US2016/044298 dated Jan. 30, 2018, 8 pages.

* cited by examiner

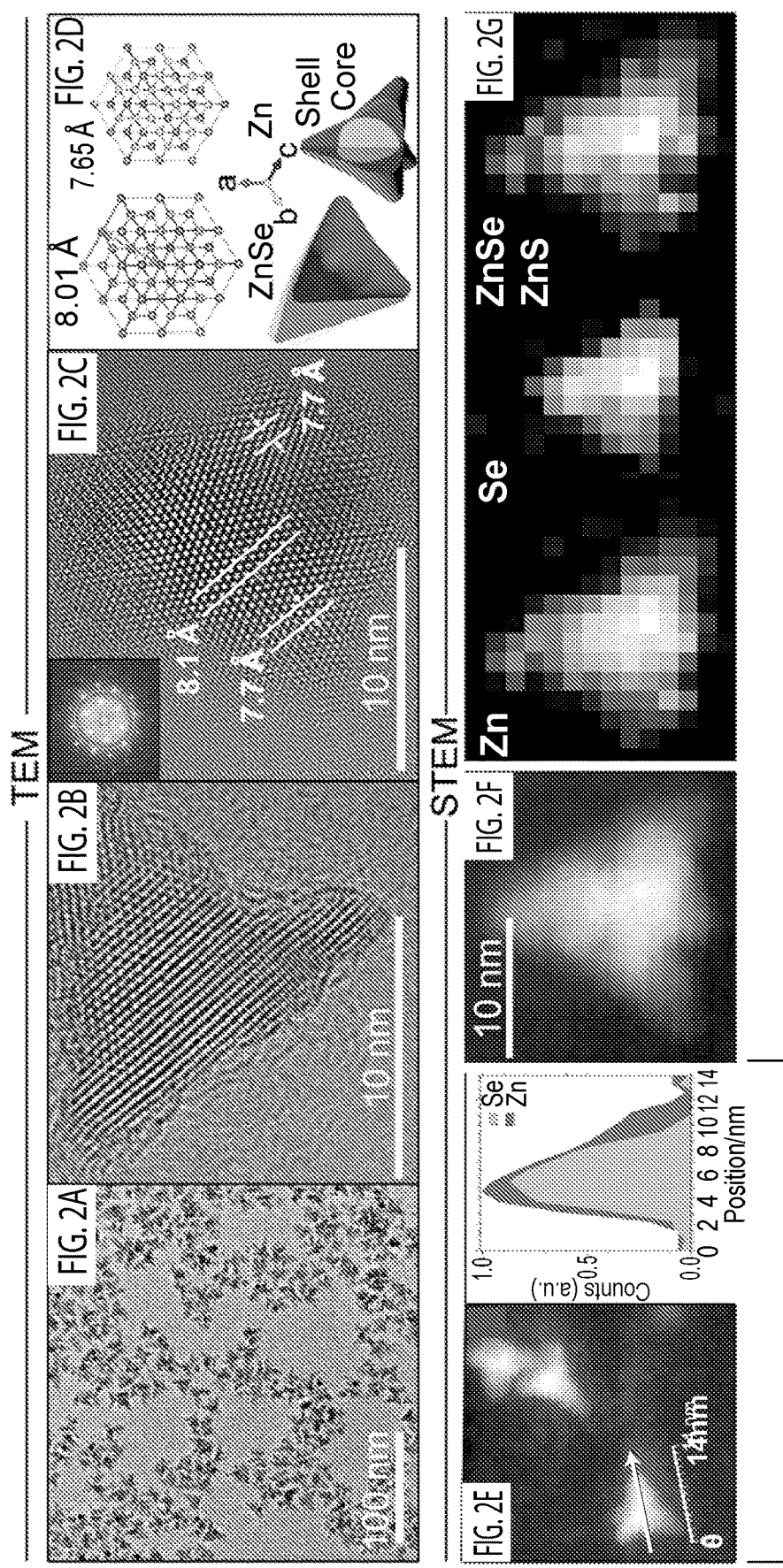

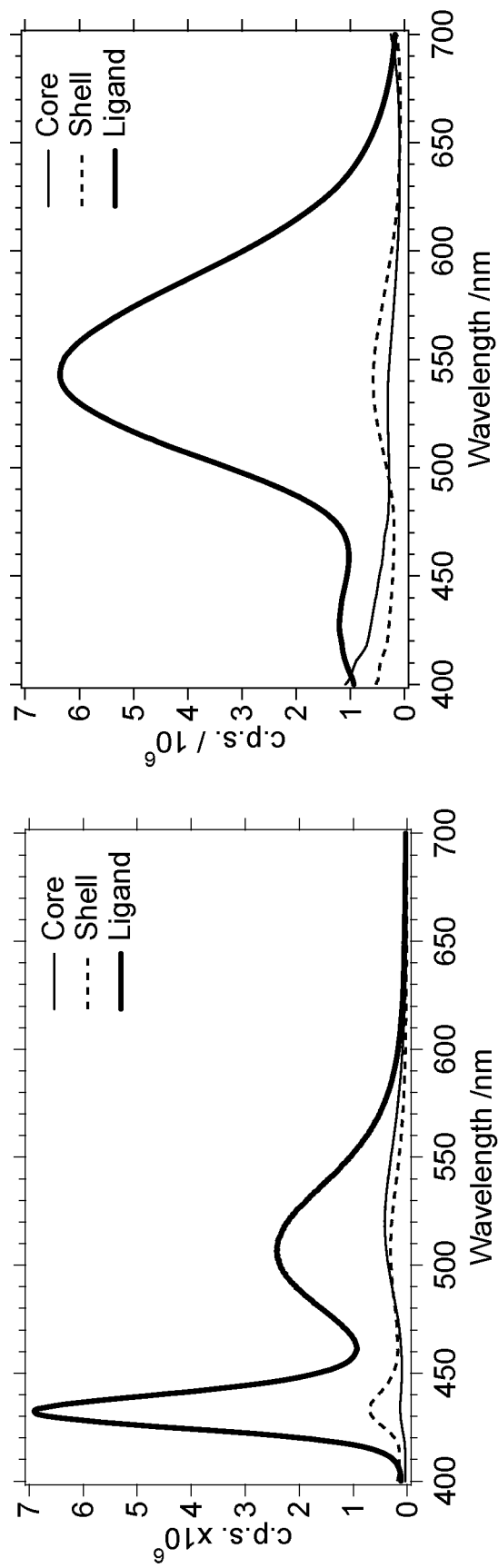

CAPPED CO-DOPED CORE/SHELL NANOCRYSTALS FOR VISIBLE LIGHT EMISSION

CROSS-REFERENCE TO RELATED APPLICATION

This application is a National Phase of International Application No. PCT/US2016/044298 filed Jul. 27, 2016, which designated the U.S. and that International Application was published under PCT Article 21(2) in English, which also includes a claim of priority under 35 U.S.C. § 119(e) to U.S. Provisional Patent Application No. 62/198,003 filed Jul. 28, 2015, the entirety of which is hereby incorporated by reference.

STATEMENT REGARDING FEDERALLY SPONSORED RESEARCH OR DEVELOPMENT

This invention was made with government support under Grant No. DE-FG02-07ER46388-A002 awarded by the United States Department of Energy. The government has certain rights in the invention.

FIELD OF THE INVENTION

The present invention generally relates to engineered materials. More specifically, the present invention relates to core/shell nanocrystals.

BACKGROUND

The following description includes information that may be useful in understanding the present invention. It is not an admission that any of the information provided herein is prior art or relevant to the presently claimed invention.

Semiconductor quantum dots (QDs) have been the subject of great interest in the past few decades as light emitting materials in a number of technologically important applications including solid-state lighting and biological labeling due to their unique electronic and optical properties which can be tuned by changing their size/shape or by doping with other elements. In these systems, stability, uniformity, tunability, efficiency, and toxicity are important considerations. Currently, CdSe-based QDs are being developed in academia and industry as next generation solid-state lighting materials due to their tunable and uniform green and red emission which arises from quantum confinement of the low bulk bandgap (1.74 eV). As such, these phosphors may be coupled to a blue emitter, like GaN or InGaN, to achieve fluorescence down conversion and white light emission or used in electroluminescent devices. However, the efficiency of a mixture of QDs for white light generation would be limited by overlap of component QD absorption and photoluminescence (PL) spectra or self-absorption from a small stokes shift and broad PL features. Furthermore, Cd pollution accumulates in waste streams and its toxicity poses serious concerns to the environment and human health. Promising alternatives to the CdSe system are doped, wide-bandgap semiconductor QDs, such as zinc chalcogenides doped with Cu, Mn, Eu, or Ga, which exhibit minimal self-absorption due to a large Stokes shift and boast reduced environmental impact. Broad spectral coverage is achievable in these II-VI semiconductor systems as doping introduces electronic states into the bandgap, allowing photo-generated carriers to relax into donor or acceptor states where they can recombine with their counterparts remaining at or near the band edge. Many such approaches have been previously reviewed. For instance, introduction of Cu as a dopant in ZnSe QDs creates an acceptor level that shifts the fluorescence from blue to green (~530 nm). However, if the dopant atoms possess different oxidation states from the host lattice atoms, single element doping can create charge imbalance that leads to compensating defects such as vacancies and/or lattice distortion. These are depicted in FIG. 1 which shows a simplified two-dimensional (2D) projection of ZnSe QDs as a model host system (top left). In a previous report, it was determined that Cu dopes the ZnSe lattice as a +1 ion, causing a compensating defect consisting of a second $Cu^+$ and a selenium vacancy ($V_{Se}^{-2}$) (FIG. 1, top right). These $V_{Se}$ defects have been identified in both ZnSe and ZnS.

With the foregoing background in mind, there is a need in the art for QDs engineered to have improved performance characteristics.

SUMMARY

The following embodiments and aspects thereof are described and illustrated in conjunction with systems, compositions and methods which are meant to be exemplary and illustrative, not limiting in scope.

The inventors have discovered inter alia that defects relating to single element doping in semiconductor materials, such as quantum dots, can be overcome by co-doping the semiconductor material with a trivalent cation. For example, as demonstrated in the Examples in the present application, doping with a single element can induce charge imbalance in the semiconductor material. This charge imbalance can be overcome by co-doping the semiconductor material with a trivalent cation, such as those selected from Group 13 elements. By co-doping with a trivalent cation, a neutral lattice with no vacancies can be achieved.

Accordingly, in one aspect, the present disclosure provides a core/shell nanocrystal comprising a core and a shell formed on the core, wherein the core/shell nanocrystal is co-doped with at least one metal dopant and at least one trivalent cation. In some embodiments, the trivalent cation is a Group 13 element.

Without limitations, the core and the surrounding shell can have distinct compositions, i.e., the core and the surrounding shell can be comprised of different materials. In some embodiments, the core comprises ZnSe and the shell comprises ZnS.

The co-doped metal dopant and the trivalent cation can be present, independently, in the core or the shell. In some embodiments, the co-doped metal and trivalent cation are present in the core. In some other embodiments, the co-doped metal and trivalent cation are present in the shell. In still some other embodiments, the co-doped metal and trivalent cation are present in both in the core and the shell. In some embodiments, the co-doped metal and trivalent cation are present only in the core.

In some embodiments, the core/shell nanocrystal further comprises a ligand. In some embodiments the ligand has the structure:

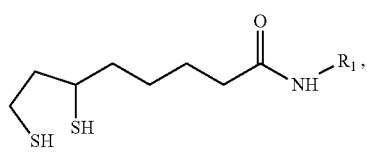

wherein $R_1$ is —$CH_2(CH_2)_7CH=CH(CH_2)_7CH_3$ or —$CH_2(CH_2)_6CH_3$. In one embodiment, $R_1$ is —$CH_2(CH_2)_7CH=CH(CH_2)_7CH_3$. In some embodiments, the above-described ligand is a capping ligand.

In various embodiments, the invention also teaches compositions comprising the above-described ligand.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2 depicts, in accordance with embodiments of the invention, TEM and STEM analysis of ZnSe/ZnS core/shell QDs. (2A) Low resolution TEM indicates that the particle dimensions are on the order of 12 nm and tetrapodal in shape. (2B) High resolution TEM of a single particle shows the high degree of crystallinity. (2C) An inverse Fourier transform (FT) image of the inset FT diffraction spots illustrates that the core is composed of ZB—ZnSe with characteristic spacing of 8.1 Å, whereas the shell material is composed of ZB—ZnS with characteristic spacing of 7.7 Å. (2D) For reference, the crystal structure of ZB—ZnSe and ZB—ZnS are shown with representative characteristic spacing labeled as indicated in (2C) as well as representative 3D models of the core/shell, tetrapod QDs. (2E) STEM images confirm the overall tetrapodal structure and the line scan spanning 14 nm from base to tip shows that Se is isolated to the QD core whereas Zn is contained throughout. (2F/2G) Drift-corrected EELS mapping of the particle shown in (2F) confirms that Se is confined to the core, supporting the assertion that the core is composed of ZnSe and the shell is composed of ZnS.

FIG. 3 depicts, in accordance with embodiments of the invention, representative PL spectra of (3A) ZnSe:Cu,Al, and (3B) ZnSe:Cu,Ga QDs before growth of the ZnS shell (Core), after the ZnS shell growth (Shell), and after the addition of the ligand (Ligand). Excitation wavelength: 380 nm.

FIG. 7 demonstrates, in accordance with embodiments of the invention, (7A) Cu EXAFS indicating the nearest neighbor distances for the probe atom in ZnSe:Cu/ZnS (Cu), ZnSe:Cu,Al/ZnS (Cu,Al), ZnSe:Cu,Ga/ZnS (Cu,Ga), and ZnSe:Cu,In/ZnS (Cu,In) compared to the Zn EXAFS. The inset of (7A) shows the expanded region highlighted by the grey box for easier viewing of the second and third neighbor peaks. (7B) Zn EXAFS of ZnSe and In EXAFS of ZnSe: Cu,In.

DESCRIPTION OF THE INVENTION

Figure 1:
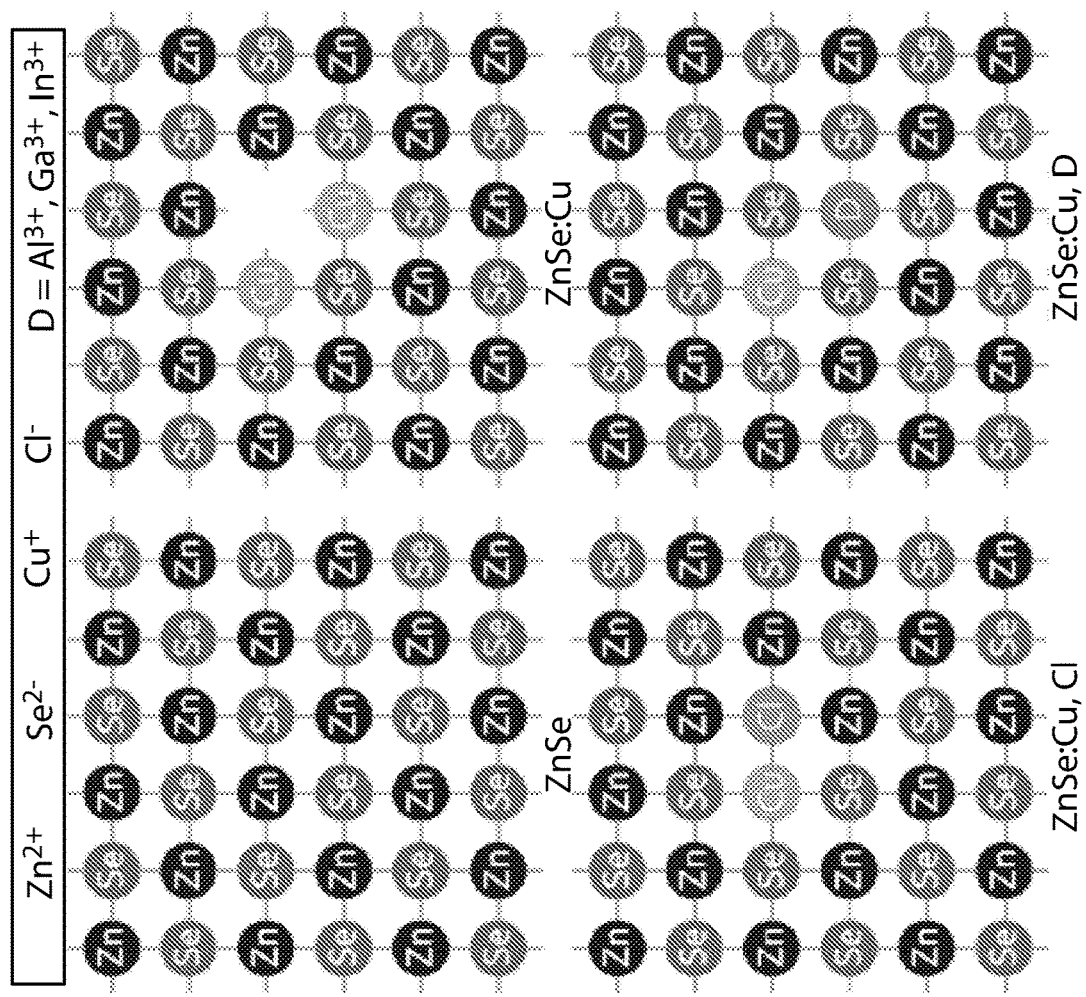
FIG. 1 depicts, in accordance with embodiments of the invention, a schematic illustration to demonstrate doping and codoping strategies in a 2D ZnSe lattice. Top left: no doping, top right: single doping with primary dopant, $Cu^+$, bottom left: codoping with oppositely charged ions, e.g. $Cl^-$, and bottom right: codoping with likely charged, trivalent ions. D represents $Al^{3+}$, $Ga^{3+}$ and $In^{3+}$.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

Described herein are the synthesis and characterization of a series of codoped core/shell ZnSe/ZnS quantum dots (QDs) with tunable PL maxima spanning 430 nm to 570 nm (FWHM=80 nm), with broad emission extending to 700 nm, through the use of $Cu^+$ as the primary dopant and trivalent cations ($Al^{3+}$, $Ga^{3+}$, and $In^{3-}$) as codopants. Additionally described is a unique thiol-based bidentate ligand that significantly improves PL intensity, long term stability, and resilience to post-synthetic processing. Through comprehensive experimental and computational studies based on spectroscopy, time-resolved PL, electron microscopy, and density functional theory (DFT), it is demonstrated that the tunable PL of this system is the result of energy level modification to donor and/or acceptor recombination pathways. By incorporating these findings with local structure information obtained from extended X-ray absorption fine structure (EXAFS) studies, a complete energetic model accounting for the photophysical processes in these unique QDs was generated. With the understanding of optical, structural, and electronic properties, this successful codoping strategy may be applied to other QD or related systems to tune the optical properties of semiconductors while maintaining relatively low toxicity, compared to Cd based QDs.

The inventors have discovered inter alia that defects relating to aliovalent single element doping in semiconductor materials, such as quantum dots, can be overcome by co-doping the semiconductor material with a trivalent cation. For example, as demonstrated in the Examples in the present application, doping with a single element can induce charge imbalance in the semiconductor material. This charge imbalance can be overcome by co-doping the semiconductor material with a trivalent cation, such as those selected from Group 13 elements. By co-doping with a trivalent cation, a neutral lattice with no vacancies can be achieved.

Various aspects disclosed herein are based on the inventors' discovery that defects relating to single element doping in semiconductor materials, such as quantum dots, can be overcome by co-doping the semiconductor material with a trivalent cation. Accordingly, in one aspect, provided herein is a core/shell nanocrystal comprising a core and a shell formed on the core, wherein the core/shell nanocrystal is co-doped with at least one metal dopant and at least one trivalent cation.

In some embodiments, the core/shell nanoparticle is a quantum dot. As used herein, the term "quantum dot" or "QD" refers to a semiconductor nanocrystal material in which excitons are confined in all three spatial dimensions. Generally, as used herein, the term "quantum dot" includes any semiconductive or metallic nanoparticle that is capable of emitting a light signal. In some embodiments, the core/shell nanoparticle is a core/shell nanocrystal. In some embodiments, the core/shell nanocrystal is a quantum dot.

It is noted that many optical, electrical and chemical properties of core/shell nanocrystals can be dependent on its size and shape. Thus, such properties can be modified or tuned by controlling the core/shell nanocrystal size. For example, the color of the light emitted by the core/shell nanocrystal depends on a number of factors that include the size and shape of the core/shell nanocrystal. A core/shell nanocrystal with a larger particle size emits light with a lower energy as compared to a core/shell nanocrystal made of the same material but with a smaller particle size.

Accordingly, without limitations, the core/shell nanocrystals described herein can be of any shape or size. For example, the shape of the core/shell nanocrystal can be spheroidal, ellipsoidal, or other geometric or non-geometric shapes. In some embodiments, the core/shell nanocrystal can be a sphere, a rod, a wire, a pyramid, or a cube. In some embodiments, the core/shell nanocrystal is spheroidal, e.g., a sphere. In some embodiments, the core/shell nanocrystal is tetrapodal.

Generally, the "size" of the core/shell nanocrystal refers to a dimension characteristic of its shape or an approximation of its shape. Accordingly, the size can be a diameter, a major axis, a predominant length, etc. Generally, the size of core/shell nanocrystals described herein is on the order of nanometers and generally ranges from 1-1000 nm. More typically, the size of the core/shell nanocrystal ranges from 1-100 nm. In some embodiments, the core/shell nanocrystal has a size in the range from 1 to 20 nm. In some embodiments, the core/shell nanocrystal has a size in the range from 7.5 nm to 17.5 nm. In some embodiments, the core/shell nanocrystal has a size in the range from 3 to 10 nm.

Without limitations, the core/shell nanocrystals can be, for example, monodispersed or polydispersed and the variation in diameter of the particles of a given dispersion can vary. In some embodiments, the core/shell nanocrystals have substantially the same size. Core/shell nanocrystals having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The core/shell nanocrystals described herein are within a narrow size distribution, thereby minimizing opportunities for contact agglomeration. "Narrow size distribution" in this context is a particle size distribution that has a ratio of the volume diameter of the 90th percentile of the small particles to the volume diameter of the 10th percentile less than or equal to 5. In some embodiments, the volume diameter of the 90th percentile of the small particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In some embodiments, the core/shell nanocrystals can be substantially spherical. "Substantially spherical" in this context means that the ratio of the lengths of the longest to the shortest perpendicular axis of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. While not wishing to be bound by one theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions.

Generally, the shell can have any desired thickness. For example, the shell can have a thickness of from about 1 nm to about 50 nm. In some embodiment, the shell has a thickness of about 1.5 nm to about 10 nm. In some preferred embodiments, the shell has a thickness of about 2 nm to about 5 nm. In some more preferred embodiments, the shell has a thickness of about 2 nm.

Generally, the absorbance and/or luminescence wavelengths of the core/shell nanocrystal are within a range from 400 nm to 700 nm. In some embodiments, the co-doped core/shell nanocrystals described herein have photoluminescence (PL) maxima in the range from 430 nm to 570 nm.

In some embodiments, co-doped core/shell nanocrystals described herein have a photoluminescent quantum yield (PL QY) of up to about 40%. In some embodiments, the co-doped semiconductor nanocrystals have a PL QY of at least about 10%. In some embodiments, core/shell nanocrystals have a PL QY ranging from about 1% to about 40%. In some embodiments, the core/shell nanocrystals have a quantum yield ranging from about 5% to about 20%.

A material for the core and/or the shell can be any material known in the art for forming core/shell nanocrystals, such as quantum dots. In other words, any semiconductor material can be used for the core and/or shell of the core/shell nanocrystals described in the present disclosure. For example, a material for the core can be selected from Group 12-16, Group 13-15 and Group 14-16 and mixtures thereof. Similarly, a material for the shell can be selected, independently of the material for the core, from Group 12-16, Group 13-15 and Group 14-16 and mixtures thereof.

In various embodiments, the core material can be selected from the group consisting of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, InAs, and any mixtures thereof. In some embodiments, the core material comprises ZnSe.

In various embodiments, the shell material can be selected from the group consisting of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, InAs, and any mixtures thereof. In some embodiments, the shell material comprises ZnS.

Exemplary metal precursors for forming the core and/or the shell of the core/shell nanocrystals include, but are not limited to, a metal oxide, a metal halide, a metal nitride, a metal ammonia complex, a metal amine, a metal amide, a metal imide, a metal carboxylate, a metal acetylacetonate, a metal dithiolate, a metal carbonyl, a metal cyanide, a metal isocyanide, a metal nitrile, a metal peroxide, a metal hydroxide, a metal hydride, a metal ether complex, a metal diether complex, a metal triether complex, a metal carbonate, a metal phosphate, a metal nitrate, a metal nitrite, a metal sulfate, a metal alkoxide, a metal siloxide, a metal thiolate, a metal dithiolate, a metal disulfide, a metal carbamate, a metal dialkylcarbamate, a metal pyridine complex, a metal bipyridine complex, a metal phenanthroline complex, a metal terpyridine complex, a metal diamine complex, a metal triamine complex, a metal diimine, a metal pyridine diimine, a metal pyrazolylborate, a metal bis(pyrazolyl) borate, a metal tris(pyrazolyl)borate, a metal nitrosyl, a metal thiocarbamate, a metal diazabutadiene, a metal dithiocarbamate, a metal dialkylacetamide, a metal dialkylformamide, a metal formamidinate, a metal phosphine complex, a metal arsine complex, a metal diphosphine complex, a metal diarsine complex, a metal oxalate, a metal imidazole, a metal pyrazolate, a metal-Schiff base complex, a metal porphyrin, a metal phthalocyanine, a metal subphthalocyanine, a metal picolinate, a metal piperidine complex, a metal pyrazolyl, a metal salicylaldehyde, a metal ethylenediamine, a metal triflate compound, or any combination thereof.

Examples of the metal precursor that can be used in formation of the core and shell of the core/shell nanocrystals include, but are not limited to, dimethyl zinc, diethyl zinc, zinc acetate, zinc stearate, zinc acetylacetonate, zinc iodide, zinc bromide, zinc chloride, zinc fluoride, zinc carbonate, zinc cyanide, zinc nitrate, zinc oxide, zinc peroxide, zinc perchlorate, zinc sulfate, dimethyl cadmium, diethyl cadmium, cadmium acetate, cadmium acetylacetonate, cadmium iodide, cadmium bromide, cadmium chloride, cadmium fluoride, cadmium carbonate, cadmium nitrate, cadmium oxide, cadmium perchlorate, cadmium phosphide, cadmium sulfate, mercury acetate, mercury iodide, mercury bromide, mercury chloride, mercury fluoride, mercury cyanide, mercury nitrate, mercury oxide, mercury perchlorate, mercury sulfate, lead acetate, lead bromide, lead chloride, lead fluoride, lead oxide, lead perchlorate, lead nitrate, lead sulfate, lead carbonate, tin acetate, tin bisacetylacetonate, tin bromide, tin chloride, tin fluoride, tin oxide, tin sulfate, germanium tetrachloride, germanium oxide, germanium ethoxide, gallium acetylacetonate, gallium acetate, gallium stearate, aluminum acetate, aluminum stearate, indium acetate, indium stearate, gallium chloride, gallium fluoride, gallium oxide, gallium nitrate, gallium sulfate, indium chloride, indium oxide, indium nitrate and indium sulfate.

Examples of the non-metal precursor that can be used in formation of the core and shell of the core/shell nanocrystals include, but are not limited to, alkyl thiol compounds (e.g., hexane thiol, octane thiol, decane thiol, dodecane thiol, hexadecane thiol and mercaptopropyl silane), sulfur-trioctylphosphine (S-TOP), sulfur-tributylphosphine (S-TBP), sulfur-diphenylphosphine (S-DPP), sulfur-phenylphosphine (S-PP), sulfur-triphenylphosphine (S-TPP), sulfur-trioctylamine (S-TOA), trimethylsilyl sulfur, ammonium sulfide, sodium sulfide, selenium-trioctylphosphine (Se-TOP), selenium-tributylphosphine (Se-TBP), selenium-phenylphosphine (Se-PP), selenium-diphenylphosphine (Se-DPP), selenium-triphenylphosphine (Se-TPP), tellurium-tributylphosphine (Te-TBP), tellurium-triphenylphosphine (Te-TPP), trimethyl silyl phosphine, alkyl phosphines (e.g., triethylphosphine, tributylphosphine, trioctylphosphine, triphenylphosphine, diphenylphosphine, phenylphosphine, and tricyclohexylphosphine), arsenic oxide, arsenic chloride, arsenic sulfate, arsenic bromide, arsenic iodide, nitric oxide, nitric acid and ammonium nitrate.

Without limitations, any metal dopant can be used in the doping of the core/shell nanocrystals. Exemplary metal dopants include, but are not limited to, transition metals, precious metals, alkali metals, and mixtures thereof. In some embodiments, the metal dopant is selected from the group consisting of Ti, Zr, Hf, V, Nb, Ta, Cr, Mo, W, Mn, Tc, Re, Fe, Ru, Os, Co, Rh, Ir, Ni, Pd, Pt, Cu, Ag, Au and any combinations thereof.

In some embodiments, the metal dopant is a transition metal. Exemplary transition metals include, but are not limited to, copper (Cu), scandium (Sc), titanium (Ti), vanadium (V), chromium (Cr), manganese (Mn), iron (Fe), cobalt (Co), nickel (Ni), and zinc (Zn). In some embodiments, the metal dopant is copper.

In some other embodiments, the metal dopant is a precious metal. Exemplary precious metals, include, but are not limited to, gold (Au), silver (Ag), platinum (Pt) and iridium (Ir). In still some other embodiments, the metal dopant is an alkali metal. Exemplary alkali metals include, but are not limited to, lithium (Li), sodium (Na), potassium (K), rubidium (Rb), cesium (Cs) and francium (Fr).

The amount of metal dopant doped into a core/shell nanocrystal varies depending on the type of dopant and the core and/or shell material. A metal dopant can be present in any desired amount in the core/shell nanocrystal. For example, the metal dopant can be present in the core/shell nanocrystal in an amount up to about 50 weight percent (atomic). In some embodiments, the metal dopant can be present in the core/shell nanocrystal in an amount ranging from about 1 weight percent to about 30 weight percent. In some embodiments, metal dopant can be present in the core/shell nanocrystal in an amount ranging from about 5 weight percent to about 20 weight percent. In some embodiments, the amount of the metal dopant in the core/shell nanocrystal is within a range from about 0.1 weight percent to about 1 weight percent.

Examples of the metal dopant precursors that can be used for preparing the core/shell nanocrystals disclosed herein include, but are not limited to: metal salts including halides, acetates, acetylacetonate or chalcogenides; and organic complex compounds.

Without limitations, the trivalent cation can be selected from Group 13 elements. For example, the trivalent cation can be $Al^{3+}$, $Ga^{3+}$, $In^{3-}$, $Tl^{3+}$, or any combinations thereof. In some embodiments, the trivalent cation is $Al^{3-}$. In some embodiments, the trivalent cation is $Ga^{3+}$. In some embodiments, the trivalent cation is $In^{3+}$. In some embodiments, the trivalent cation is $Tl^{3+}$. In some embodiments, the trivalent cation can be $Al^{3+}$, $Ga^{3+}$, $In^{3-}$, or any combinations thereof. In some embodiments, the trivalent cation is a Group 13 trivalent cation.

The amount of trivalent cation doped into a core/shell nanocrystal can vary depending on the type of the trivalent cation, metal dopant and the core and/or shell material. A trivalent cation can be present in any desired amount in the core/shell nanocrystal. For example, the trivalent cation can be present in the core/shell nanocrystal in an amount up to about 50 weight percent (atomic). In some embodiments, the trivalent cation can be present in the core/shell nanocrystal in an amount ranging from about 1 weight percent to about 30 weight percent. In some embodiments, trivalent cation can be present in the core/shell nanocrystal in an amount ranging from about 5 weight percent to about 20 weight percent. In some embodiments, the amount of the trivalent cation in the core/shell nanocrystal is within a range from about 0.1 weight percent to about 1 weight percent.

Further, the metal dopant and the trivalent cation can be doped into the core/shell nanocrystals in about equal amounts. In many embodiments, the metal dopant and the trivalent cation are present in about equal atomic weight percent in the core/shell nanocrystals.

In some embodiments, the core/shell nanocrystal further comprises a passivation shell formed on the core/shell nanocrystal. Generally, the passivation shell is composed of a material that has band gaps greater than those of the shell material or a material that has a lower oxidation tendency. Based on the passivation effect that is caused by the passivation shell, the luminescence property of the core/shell nanocrystal can be maintained and the luminescence efficiency of the core/shell nanocrystal can be further improved owing to quantum confinement effects.

A material for the passivation shell is not particularly limited. For example, the material for the passivation shell can be selected from Group 12-16, Group 13-15 and Group 14-16 and mixtures thereof. Further, the material for the passivation shell can be same as the core material and/or the shell material but without any dopants. Accordingly, in some embodiments, the material for the passivation shell is same as the core but without any dopant material that can be present in the core. In some other embodiments, the material for the passivation shell is same as the shell but without any dopant material that can be present in the shell.

In various embodiments, the passivation shell material can be selected from the group consisting of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, InAs, and any mixtures thereof. In some embodiments, the passivation shell material comprises ZnS.

The core/shell nanocrystals can also include ligands or can be functionalized with other chemical moieties for a specific purpose. In some embodiments, the ligand is thiol-based bidentate ligand. For example, a ligand comprising at least two thiol groups (i.e., two SH or S⁻ groups) and wherein the ligand is hydrophobic group. As used herein, the term "hydrophobic" refers to a molecular entity that tends to be non-polar and, thus, prefers other neutral molecules and non-polar solvents.

In some embodiments, the ligand is a dihydrolipoic acid (6,8-dimercaptooctanoic acid) conjugated with a hydrophobic molecule. In some embodiments, the ligand is a lipoic acid (6,8-Dithiooctanoic acid). For example, the ligand can be a dihydrolipoic acid conjugated via an ester or amide linkage to a hydrophobic molecule. In some embodiments, the ligand is a dihydrolipoic acid conjugated via an ester or amide linkage to a molecule comprising from about 8 carbons to about 20 carbons. In some embodiments, the ligand is a dihydrolipoic acid conjugated via an ester or amide linkage to a hydrophobic molecule comprising from about 10 carbons to about 20 carbons, preferably 15 to 18 carbons.

In some embodiments, the ligand is of structural Formula I:

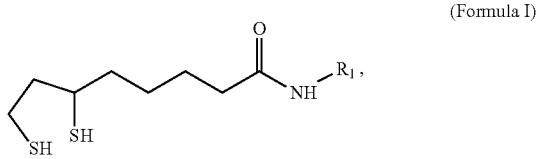

(Formula I)

wherein $R_1$ is $C_8$-$C_{20}$ alkyl, $C_8$-$C_{20}$ alkenyl, $C_8$-$C_{20}$ alkynyl, each of which can be optionally substituted.

In some embodiments, $R_1$ is $-CH_2(CH_2)_7CH=CH(CH_2)_7CH_3$ or $-CH_2(CH_2)_6CH_3$. In one embodiment, $R_1$ is $-CH_2(CH_2)_7CH=CH(CH_2)_7CH_3$. In one embodiment, $R_1$ is $-CH_2(CH_2)_6CH_3$.

The present disclosure also provides a composition comprising a compound of Formula I. In some embodiments, the composition comprising the compound of Formula I is a core/shell nanocrystal comprising a core and a shell formed on the core, wherein the core/shell nanocrystal is doped with at least one metal dopant. Without limitations, a core/shell nanocrystal can be a core/shell nanocrystal that is only doped with a metal dopant and is not co-doped with a trivalent cation. In some embodiments, the composition comprising the compound of Formula I is a quantum dot. In some embodiments, the composition comprising the compound of Formula I is a core/shell nanocrystal comprising a core and a shell formed on the core, wherein the core/shell nanocrystal is co-doped with at least one metal dopant and at least one trivalent cation. In some embodiments, the composition comprising the compound of Formula I is a core/shell nanocrystal comprising a core, a shell formed on the core, and a passivation shell formed on the shell, wherein the core/shell nanocrystal (i) is only doped with a metal dopant and is not co-doped with a trivalent cation, or (ii) is co-doped with at least one metal dopant and at least one trivalent cation.

The co-doped core/shell nanocrystals described herein can be prepared by any method known to one of skill in the art for preparing core/shell nanocrystal materials. An exemplary method of preparing the co-doped core/shell nanocrystals described herein is described in the Examples section of the present application.

The co-doped core/shell nanocrystals described herein can be utilized in any of the applications quantum dots are used. For example, uses for the co-doped core/shell nanocrystals described herein include, but are not limited to, biological labeling, diagnostics, display sensors, energy fields, light emitting devices, photovoltaic devices, and photodetector devices. Additional uses for the co-doped core/shell nanocrystals described herein include, but are not limited to, solid state lighting, electroluminescent devices, light emitting materials.

In some embodiments, the present invention provides a core/shell nanocrystal, comprising a core; and a shell formed on a surface of the core, wherein the core/shell nanocrystal is co-doped with at least one metal dopant and at least one Group 13 trivalent cation. In some embodiments, the present invention provides a core/shell nanocrystal, comprising a core; a shell formed on a surface of the core, wherein the core/shell nanocrystal is co-doped with at least one metal dopant and at least one Group 13 trivalent cation; and a capping ligand, wherein the capping ligand is attached to a surface of the shell. In some embodiments, the present invention provides a core/shell nanocrystal, comprising a core; a shell formed on a surface of the core, wherein the core/shell nanocrystal is co-doped with at least one metal dopant and at least one Group 13 trivalent cation; and a passivation shell formed on a surface of the shell. In some embodiments, the present invention provides a core/shell nanocrystal, comprising a core; a shell formed on a surface of the core, wherein the core/shell nanocrystal is co-doped with at least one metal dopant and at least one Group 13 trivalent cation; a passivation shell formed on a surface of the shell; and a capping ligand, wherein the capping ligand is attached to a surface of the shell, the passivation shell or both. In some embodiments, the at least one metal dopant and the at least one Group 13 trivalent cation are present in the core, the shell, or both. In some embodiments, the core is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; and the shell is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof. In some embodiments, the core is comprised of ZnSe; and the shell is comprised of ZnS. In some embodiments, the at least one metal dopant is a transition metal. In some embodiments, the at least one metal dopant is $Cu^{2+}$. In some embodiments, the at least one Group 13 trivalent cation is selected from $Al^{3-}$, $Ga^{3+}$, $In^{3+}$, and any combinations thereof. In some embodiments, the at least one Group 13 trivalent cation is $Al^{3+}$. In some embodiments, the at least one Group 13 trivalent cation is $Ga^{3+}$. In some embodiments, the at least one Group 13 trivalent cation is $In^{3-}$. In some embodiments, the at least one metal dopant is $Cu^{2+}$; and the at least one Group 13 trivalent cation is selected from $Al^{3+}$, $Ga^{3-}$, and $In^{3+}$. In some embodiments, the capping ligand has the structure:

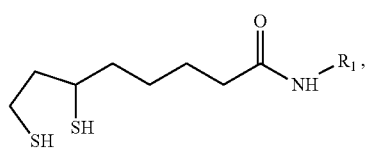

wherein $R_1$ is —$CH_2(CH_2)_7CH=CH(CH_2)_7CH_3$ or —$CH_2(CH_2)_6CH_3$. In some embodiments, the capping ligand has the structure:

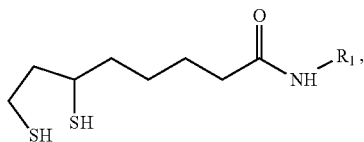

wherein $R_1$ is —$CH_2(CH_2)_7CH=CH(CH_2)_7CH_3$. In some embodiments, the core/shell nanocrystal is a quantum dot.

In some embodiments, the present invention provides a method of making a core/shell nanocrystal comprising a core and a shell, the method comprising forming the core; and forming the shell on a surface of the core so as to make the core/shell nanocrystal, wherein the core/shell nanocrystal is co-doped with at least one metal dopant and at least one Group 13 trivalent cation. In some embodiments, the present invention provides a method of making a core/shell nanocrystal comprising a core and a shell, the method comprising forming the core, forming the shell on a surface of the core so as to make the core/shell nanocrystal, wherein the core/shell nanocrystal is co-doped with at least one metal dopant and at least one Group 13 trivalent cation, and attaching a capping ligand to a surface of the shell. In some embodiments, the present invention provides a method of making a core/shell nanocrystal comprising a core and a shell, the method comprising forming the core, forming the shell on a surface of the core so as to make the core/shell nanocrystal, wherein the core/shell nanocrystal is co-doped with at least one metal dopant and at least one Group 13 trivalent cation, and forming a passivation shell on a surface of the shell. In some embodiments, the present invention provides a method of making a core/shell nanocrystal comprising a core and a shell, the method comprising forming the core, forming the shell on a surface of the core so as to make the core/shell nanocrystal, wherein the core/shell nanocrystal is co-doped with at least one metal dopant and at least one Group 13 trivalent cation, forming a passivation shell on a surface of the shell, and attaching a capping ligand to a surface of the shell, the passivation shell or both. In some embodiments, the at least one metal dopant and the at least one Group 13 trivalent cation are present in the core, the shell, or both. In some embodiments, the core is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; and the shell is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof. In some embodiments, the core is comprised of ZnSe; and the shell is comprised of ZnS. In some embodiments, the at least one metal dopant is a transition metal. In some embodiments, the at least one metal dopant is $Cu^{2+}$. In some embodiments, the at least one Group 13 trivalent cation is selected from $Al^{3-}$, $Ga^{3+}$, $In^{3+}$, and any combinations thereof. In some embodiments, the at least one Group 13 trivalent cation is $Al^{3+}$. In some embodiments, the at least one Group 13 trivalent cation is $Ga^{3+}$. In some embodiments, the at least one Group 13 trivalent cation is $In^{3+}$. In some embodiments, the at least one metal dopant is $Cu^{2-}$; and the at least one Group 13 trivalent cation is selected from $Al^{3+}$, $Ga^{3+}$, and $In^{3+}$. In some embodiments, the capping ligand has the structure:

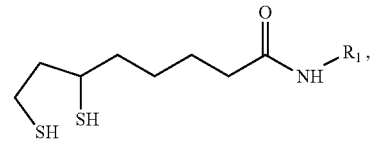

wherein $R_1$ is —$CH_2(CH_2)_7CH=CH(CH_2)_7CH_3$ or —$CH_2(CH_2)_6CH_3$. In some embodiments, the capping ligand has the structure:

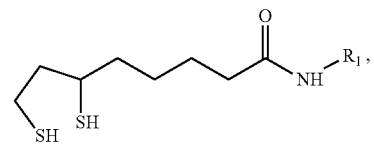

wherein $R_1$ is —$CH_2(CH_2)_7CH=CH(CH_2)_7CH_3$. In some embodiments, the core/shell nanocrystal is a quantum dot. In some embodiments, the present invention provides a core/shell nanocrystal made according to any of the methods described herein.

In some embodiments, the present inventions provides a compound having the structure:

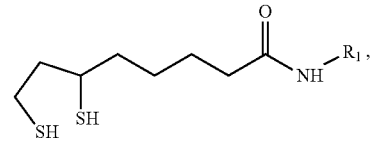

wherein $R_1$ is —$CH_2(CH_2)_7CH=CH(CH_2)_7CH_3$ or —$CH_2(CH_2)_6CH_3$. In some embodiments, the present invention provides a composition comprising a compound having the structure:

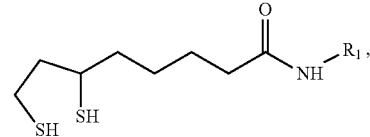

wherein $R_1$ is —$CH_2(CH_2)_7CH=CH(CH_2)_7CH_3$ or —$CH_2(CH_2)_6CH_3$. In some embodiments the composition is a core/shell nanocrystal. In some embodiments, the composition is a quantum dot.

In some embodiments, the present invention provides a core/shell nanocrystal according to the invention for use in biological labeling, diagnostics, display sensors, energy fields, light emitting devices, photovoltaic devices, photodetector devices, solid state lighting, electroluminescent devices, or light emitting materials.

The disclosure is further illustrated by the following examples which should not be construed as limiting. The examples are illustrative only, and are not intended to limit, in any manner, any of the aspects described herein.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Structural, Electronic, and Optical Properties of Core/Shell ZnSe:Cu$^+$/ZnS Quantum Dots Codoped with Al$^{3+}$, Ga$^{3+}$ and In$^{3+}$ Surface Passivation, Structure, and Morphology In order to address the common issues of low PL yield and long-term instability, a two-pronged approach was developed to passivate surface dangling bonds. First, a ZnS shell was added to insulate both the electron and the hole and confine them to the ZnSe core. After shell addition, transmission electron microscopy (TEM) reveals the resultant tetrapodal shape and high monodispersity (FIG. 2A).

Figure 11:
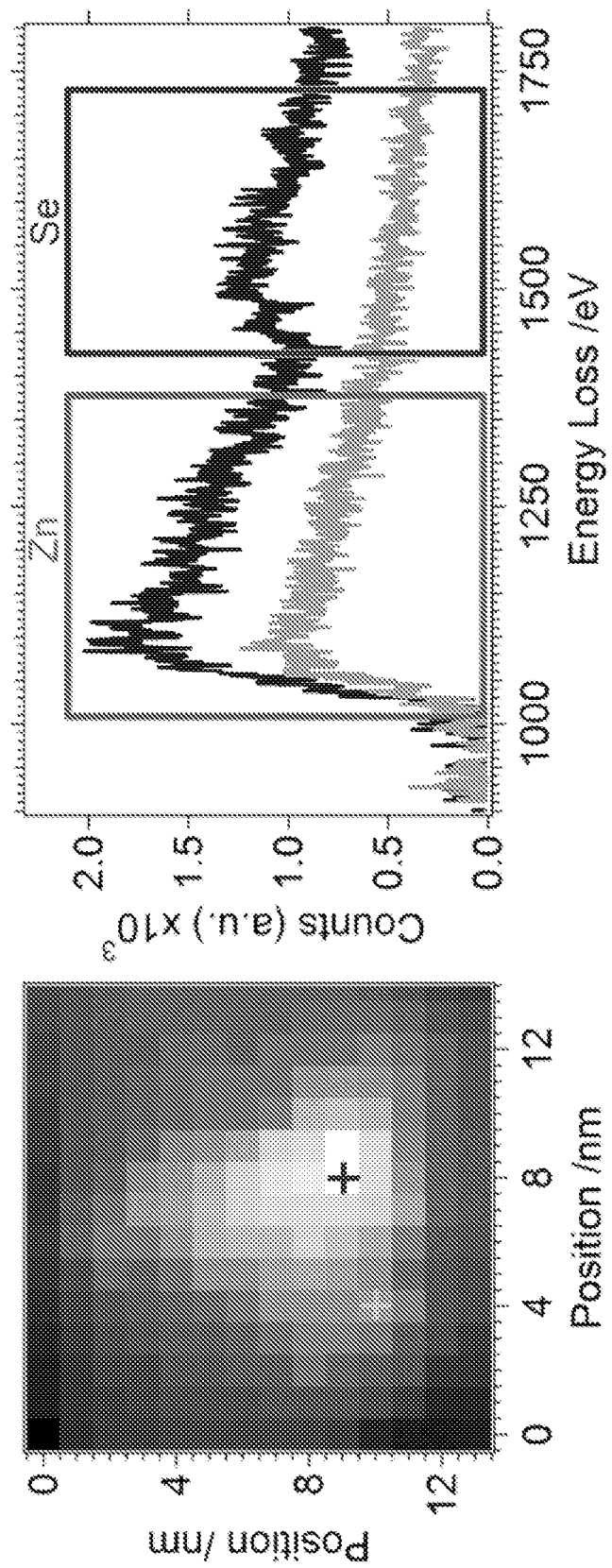
FIG. 11 depicts, in accordance with embodiments of the invention, drift-corrected STEM-EELS mapping of a single ZnSe/ZnS QD. STEM image (left) and corresponding electron energy loss spectra highlighting the onset of the Zn peak (1020 eV) and Se peak (1430 eV). The black cross and corresponding black spectrum represent an energy loss measurement of the core region while the gray cross and corresponding gray spectrum represent an energy loss measurement of the shell region. While Zn was detected in both regions, Se was detected only in the core region. This supports the assignment of a ZnSe core and ZnS shell.

The tetrapods extend ~12 nm from base to tip and are single crystalline in nature (FIG. 2B). Furthermore, the inverse Fourier transform (FT) of a high resolution TEM image of a single QD reveals lattice spacing measurements that support the core/shell structure (FIG. 2C). The spacing of 8.1 Å in the core region and 7.7 Å in the shell region correspond well with those expected for the zinc blende (ZB) crystal structures of ZnSe and ZnS, respectively (FIG. 2D). Three-dimensional (3D) models of the core/shell tetrapods are shown as visualization aids (bottom of FIG. 2D). The QD structure was also studied by scanning TEM (STEM) where the tetrapodal shape is more apparent (FIG. 2E). To corroborate the assignments gleaned from lattice spacing measurements, the elemental composition was collected as a function of position across one arm of a tetrapod by combining STEM with electron energy loss spectroscopy (EELS) (FIG. 2E). The scan spanned 14 nm in the base to tip direction indicated by the red arrow. Zn is found throughout the length of the particle whereas Se is confined to the core region; a sulfur signal could not be isolated from the large carbon-related background signal. This spatial assignment was further confirmed through elemental mapping of an entire particle (FIG. 2F/2G). The EELS spectrum at two points, representing the core and shell regions, is provided in FIG. 11. These analyses support that the core is composed of ZnSe (~8 nm) while the shell is composed of ZnS (~2 nm).

Improved Photoluminescence (PL) Yield and Stability with Custom Designed Capping Ligand Complete confinement is not always realized after shell addition as tunneling and Fermi level alignment may allow the photoelectron to travel into the shell where it is again susceptible to surface trapping from dangling bonds. As such, a custom bidentate, thiol-based capping ligand was designed and incorporated as a second measure to ensure complete electronic surface passivation. It should be noted that using surfactants and ligands that bind weakly with the impurity atoms is a prerequisite for doping, as strongly-bound ligands hinder the adsorption and subsequent doping of the impurity atoms. However, typical post-synthetic processing, including cleaning of ZnSe QDs from the crude reaction mixture, can be quite challenging and often results in complete quenching of the PL due to the loss of the weakly bound capping ligand or oxidation. Therefore, the weak binding octadecylamine ligand was used initially to ensure efficient doping of the core, but exchanged with the inventive strong binding thiol-based ligand after doping in order to fortify the QDs against typical cleaning conditions. The new ligand was synthesized by modifying lipoic acid, the procedure for which is shown in Scheme 1. Lipoic acid is often used in aqueous synthesis methods or in ligand exchange to improve water solubility. Since water solubility was not desired here, the acidic functional group of lipoic acid was instead used to attach oleylamine and create a hydrophobic backbone. This approach was also pursued in order to improve intermolecular ligand stabilization through backbone hydrogen-bonding of neighboring ligands by way of the amide bond.

Scheme 1: Reaction mechanism for the synthesis of the custom capping ligand.

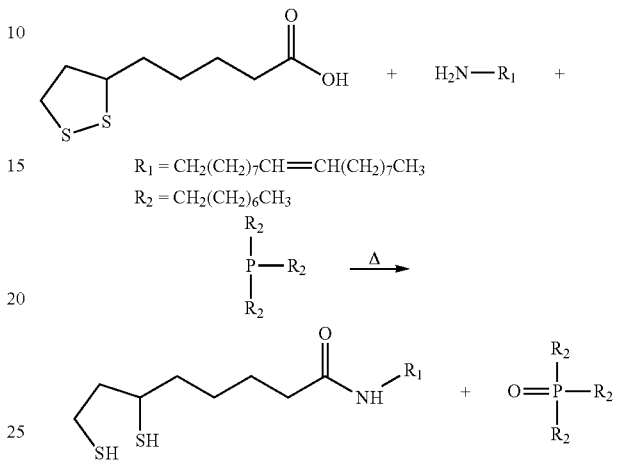

The PL of the QDs at each stage of modification is compared in FIG. 3 for two representative samples, ZnSe:Cu,Al/ZnS (Cu,Al) (FIG. 3A) and ZnSe:Cu,Ga/ZnS (Cu,Ga) (FIG. 3B). The samples were prepared at the same optical density at the wavelength of excitation, 380 nm (3.26 eV). Prior to shell addition, both samples displayed relatively low PL and emission could barely be detected by the naked eye. Also, very weak host emission could be seen for ZnSe:Cu,Al. After the ZnS shell was added, the PL for both samples was seen to slightly improve. Addition of the bidentate capping ligand resulted in more complete surface passivation of the dangling bonds and a 10-fold improvement in integrated PL intensity. While not wishing to be bound by a single theory, this effect suggests that the ZnS shell alone was an incomplete insulator for the ZnSe core when considering the photoexcited-electron. Alternatively, it could indicate incomplete coverage of the ZnSe core by the ZnS shell. Either way, after the capping ligand addition, dangling bonds at the ZnS surface and any remaining ZnSe surfaces were more completely passivated, resulting in reduced surface trapping and a dramatic improvement in PL yield. As desired, the ZnSe/ZnS system retained excellent PL even after being washed several times, crashed out of solution, stored, and resuspended in chloroform.

Figure 12B:
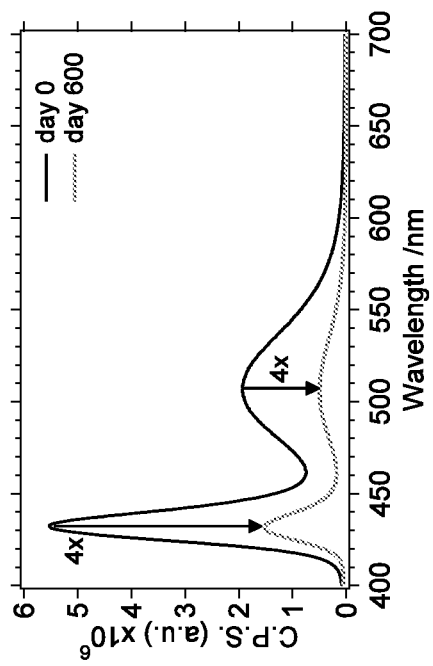
FIG. 12 depicts, in accordance with embodiments of the invention, the PL spectrum of the ZnSe:Cu,Al/ZnS (12A) and ZnSe:Cu,Ga/ZnS (12B) QD samples initially and after 600 and 620 days of storage in dichloromethane at ~−10° C. A reduction of 4× and 5× was observed in the two samples, respectively. No shift in the PL spectrum or line shape was observed.
Figure 12A:
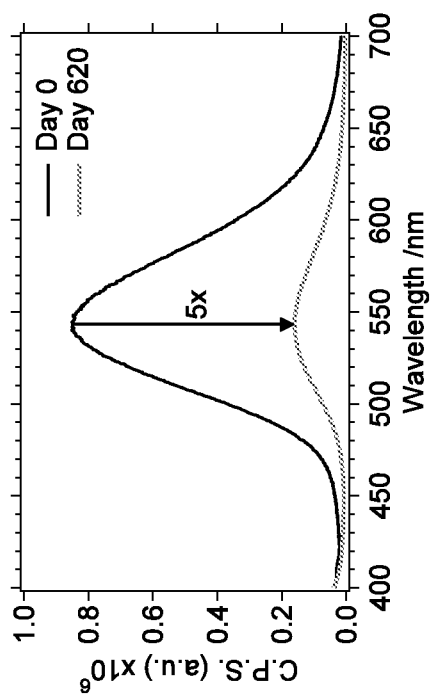

For long term storage, the QDs were dispersed in dichloromethane (DCM) and stored in a freezer. The PL collected on the Cu,Al and Cu,Ga samples after storing for 600 and 620 days show a 4 and 5× reduction in integrated PL intensity, respectively, as compared to 0 days (the day of synthesis) FIG. 12. No shift in the PL position or line shape was observed in either sample indicating the long-term stability of the emission profile. Overall, the increased PL yield and robustness of the resultant product as a result of the ZnS shell and ligand addition represent significant achievements in ZnSe QD synthesis, which is important for practical applications of such QDs.

It is clear from these results that adequate surface passivation is not only important for yield and stability, but also important for observing emission processes that may otherwise be suppressed by surface trapping or other non-radiative recombination processes. For instance, the host-related band edge PL (440 nm) in the Cu,Al system was not seen in a previous report and is also not seen for the bare ZnSe:Cu,Al core shown in FIG. 3A. However, host related emission becomes increasingly apparent after the addition of the ZnS shell and even more pronounced with the combination of shell and ligand. Band-edge PL is allowed so long as the VB photogenerated hole and the CB electron are not trapped by the surface, making this recombination much more sensitive to surface quality. As such, competing pathways such as surface trapping may serve to reduce the host emission disproportionally compared to the Cu-related emission. The Cu-related emission in this system occurs through recombination of the VB electron to the hole bound to the Cu acceptor state. Strong localization at the Cu acceptor provides stabilization of the Cu-related recombination mechanism even with surface trapping of the photohole present in the core sample. For this reason, Cu-related emission is seen for all stages of the synthesis. It should be noted that for the Cu,Ga sample, very little host emission was observed at any stage of the reaction. Further details regarding the emission mechanism which describe this observation are provided below. Briefly, it is due to localization of the photoelectron at a Ga-related donor state. The combination of hole and electron localization at Cu and Ga centers diminishes the host-related PL. The PL intensity, however, is still affected due to lost flux of photogenerated species toward non-radiative pathways at the surface.

Optical Properties of the Codoped Quantum Dots

Figure 4A:
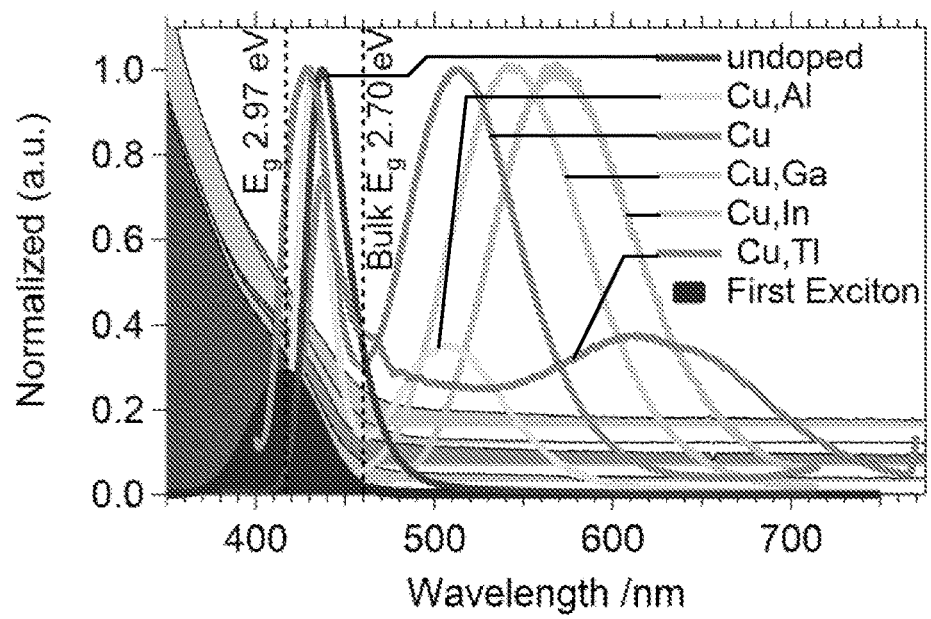
FIG. 4 depicts, in accordance with embodiments of the invention, (4A) Normalized absorption and PL spectra ($\lambda_{ex}$=380 nm) of undoped ZnSe/ZnS (undoped), ZnSe:Cu, Al/ZnS (Cu,Al), ZnSe:Cu/ZnS (Cu), ZnSe:Cu,Ga/ZnS (Cu, Ga) and ZnSe:Cu,In/ZnS (Cu,In). Absorption spectra are shown as filled curves and PL spectra are shown as solid lines. Absorption spectra are offset for clarity. $E_g$ and Bulk $E_g$ represent the absorption onset of the ZnSe/ZnS QDs and bandgap of bulk ZnSe, respectively. (4B) Photograph of the codoped ZnSe/ZnS QD system as excited by UV light. (4C) CIE 1976 chromaticity plot showing the PL spectra from (4A) mapped onto the u',v' color space. Also indicated is the equal-energy radiator 'E'.

To assess the extent of tunability and possible self-absorption, the optical properties were investigated with UV-Vis absorption and PL spectroscopies. The UV-Vis spectra of undoped ZnSe/ZnS (undoped), singly-doped ZnSe:Cu/ZnS (Cu), and codoped ZnSe:Cu,Al/ZnS (Cu,Al), ZnSe:Cu,Ga/ZnS (Cu,Ga), and ZnSe:Cu,In/ZnS (Cu,In) core/shell QDs are shown in FIG. 4A and are vertically offset for clarity. No change in absorption was observed with the inclusion of the primary dopant ($Cu^+$) or codopants ($Al^{3+}$, $Ga^{3+}$, or $In^{3+}$); the absorption onsets of all the samples occurred at the same energy, 2.97 eV (417 nm), demonstrating the high degree of uniformity of the core size from batch to batch. The Gaussian fit of the first exciton absorption band, which applies to all the samples studied, is also indicated for clarity. Considering the Bohr exciton radius of bulk ZnSe is 4.5 nm, the optical properties of the QDs are expected to be affected by quantum confinement. Indeed, the absorption onsets (indicated as $E_g$) are blue-shifted from that of bulk ZnSe (indicated as Bulk $E_g$), which has a bandgap of 2.70 eV (460 nm) at room temperature. Zinc blende-ZnS has a bulk bandgap of 3.68 eV (337 nm) and, as such, no contribution from the ZnS shell could be resolved for the samples in the spectral region studied.

Figure 13:
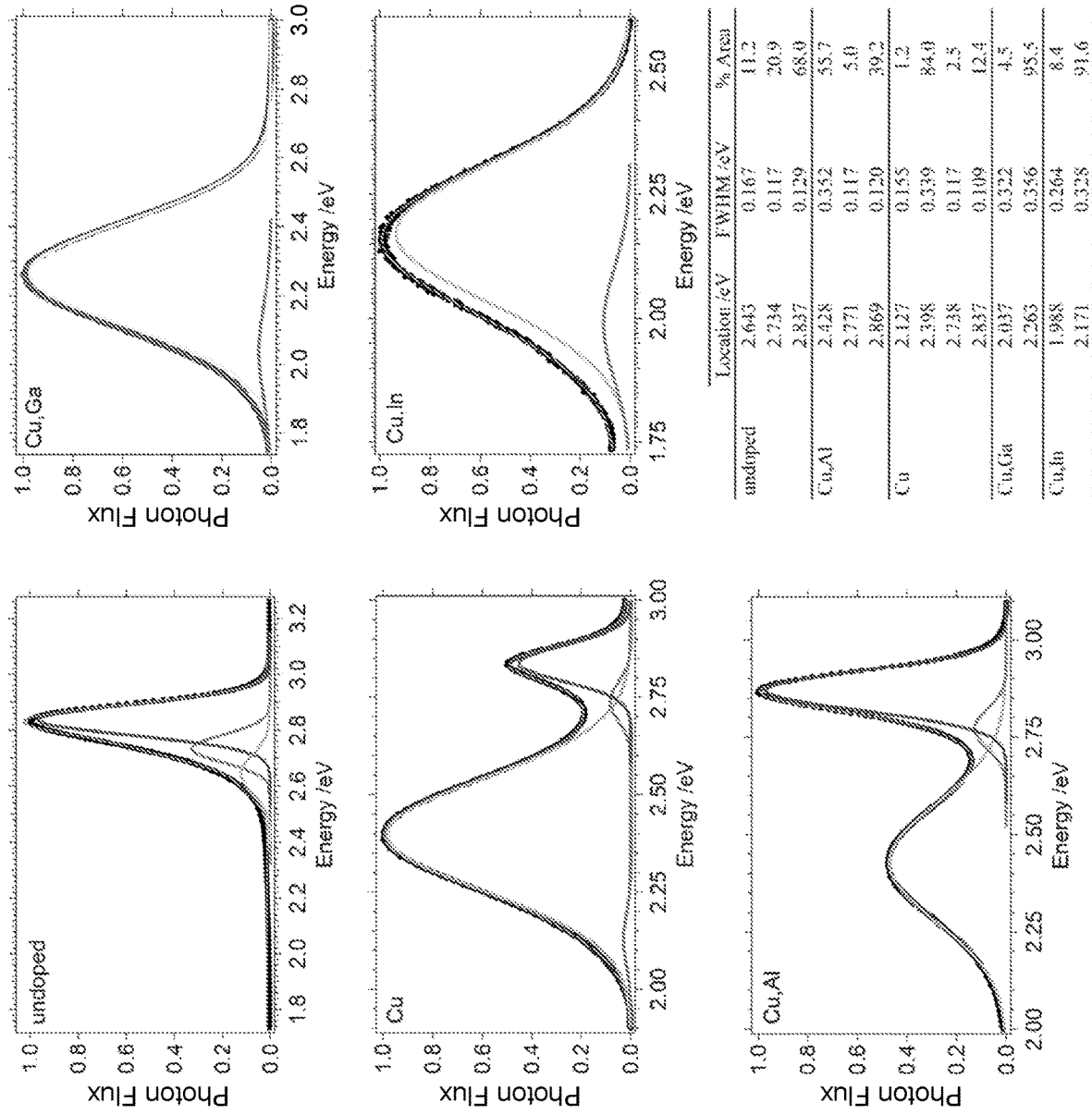
FIG. 13 depicts, in accordance with embodiments of the invention, Gaussian fitting analysis of the photoluminescence spectra of ZnSe/ZnS (undoped), ZnSe:Cu/ZnS (Cu), ZnSe:Cu,Al/ZnS (Cu,Al), ZnSe:Cu,Ga/ZnS (Cu,Ga), and ZnSe:Cu,In/ZnS (Cu,In) QDs. The fitting results for location (eV), full width at half max (FWHM), and relative area (% area) are tabulated as well.

The corresponding PL spectra are shown as solid lines in FIG. 4A. The spectra are transformed to photon flux vs. photon energy using Equation 1, where $I_0(\lambda)$ is PL intensity as a function of wavelength, and subsequently fit with multi-Gaussian fitting, as shown in FIG. 13. The average FWHM was 80 nm for the doped samples. The relative integrated area of the spectral components is also provided.

$$I_0(\lambda)d\lambda = \frac{\lambda^2 I_0}{1240 \; ev.num} dE \quad (1)$$

Figure 4B:
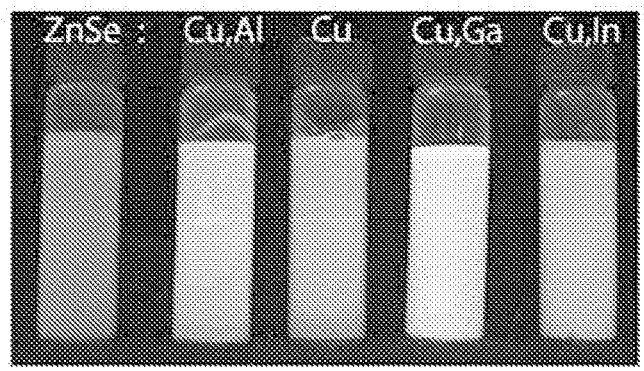

The undoped sample has a prominent band edge emission in the blue, centered at 437 nm. After incorporation of $Cu^+$ into the ZnSe core, a new emission peak in the green is observed at 517 nm, along with residual host (ZnSe) band edge emission at 436 nm. Introducing $Al^{3+}$ as a codopant results in a green emission band centered at 509 nm but increased host emission at 432 nm. The increased host emission is attributed to decreased charge-compensating defect formation (i.e. $V_{Se}^{2-}$), which acts to red shift the PL in the singly-doped system. With a $Ga^{3+}$ codopant, the PL was shifted significantly to the red and resulted in very clean yellow emission by eye, centered at 550 nm. The host emission observed in the previous samples was completely eliminated. Finally, In codoping resulted in the largest red shift of all the samples, with PL centered at 570 nm, which also showed no evidence of host-related emission. A photograph of the samples as illuminated by UV light illustrates the blue to orange PL span of this ZnSe system (FIG. 4B). It should be noted that the absorption and PL regions are significantly distinct due to the large Stokes shift, allowing the ZnSe/ZnS QD system to avoid efficiency losses due to self-absorption. Experiments were conducted to include a $Tl^{3+}$ codopant to further red-shift PL to ~635 nm (FIG. 14), but its incorporation into the host lattice was severely limited by its relatively large size, resulting in incomplete doping and poor overall PL uniformity.

Figure 4C:
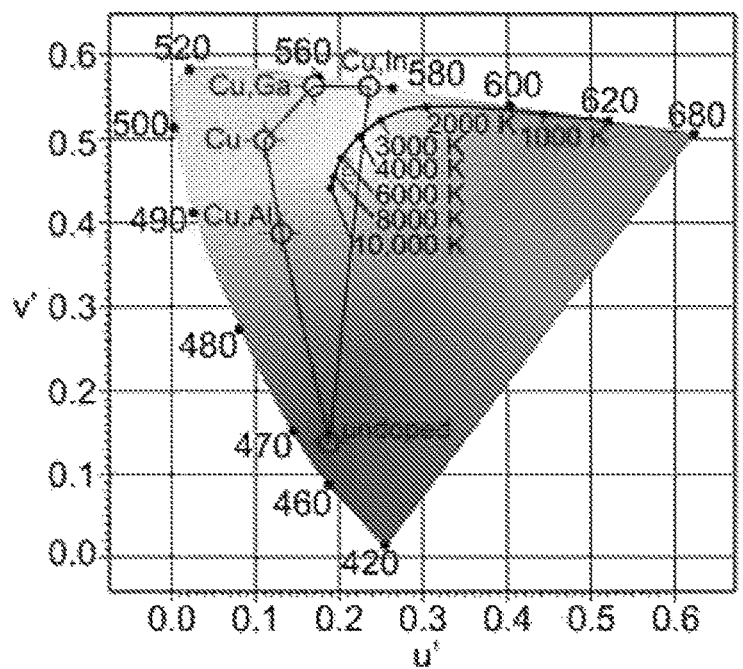

Using the CIE (International Commission on Illumination) 1976 chromaticity coordinates, the combination of the undoped and Cu,In QDs could generate white light with an approximately 4,000 K color temperature, as shown in FIG. 4C. For reference, incandescent light is 2,800 K, halogen light is 3,000 K, and direct sunlight is 4,800 K. However, mixtures of the reported QD systems herein could achieve cooler white light color temperatures; decreasing the quantum confinement in the Cu,In system is expected to red shift the PL and lower the potential color temperature further. Therefore, these QDs are promising for application in next generation white light QD-LED technologies.

Reduced Trap State Emission with Codoping and Quantum Yield Determination

Figure 15A:
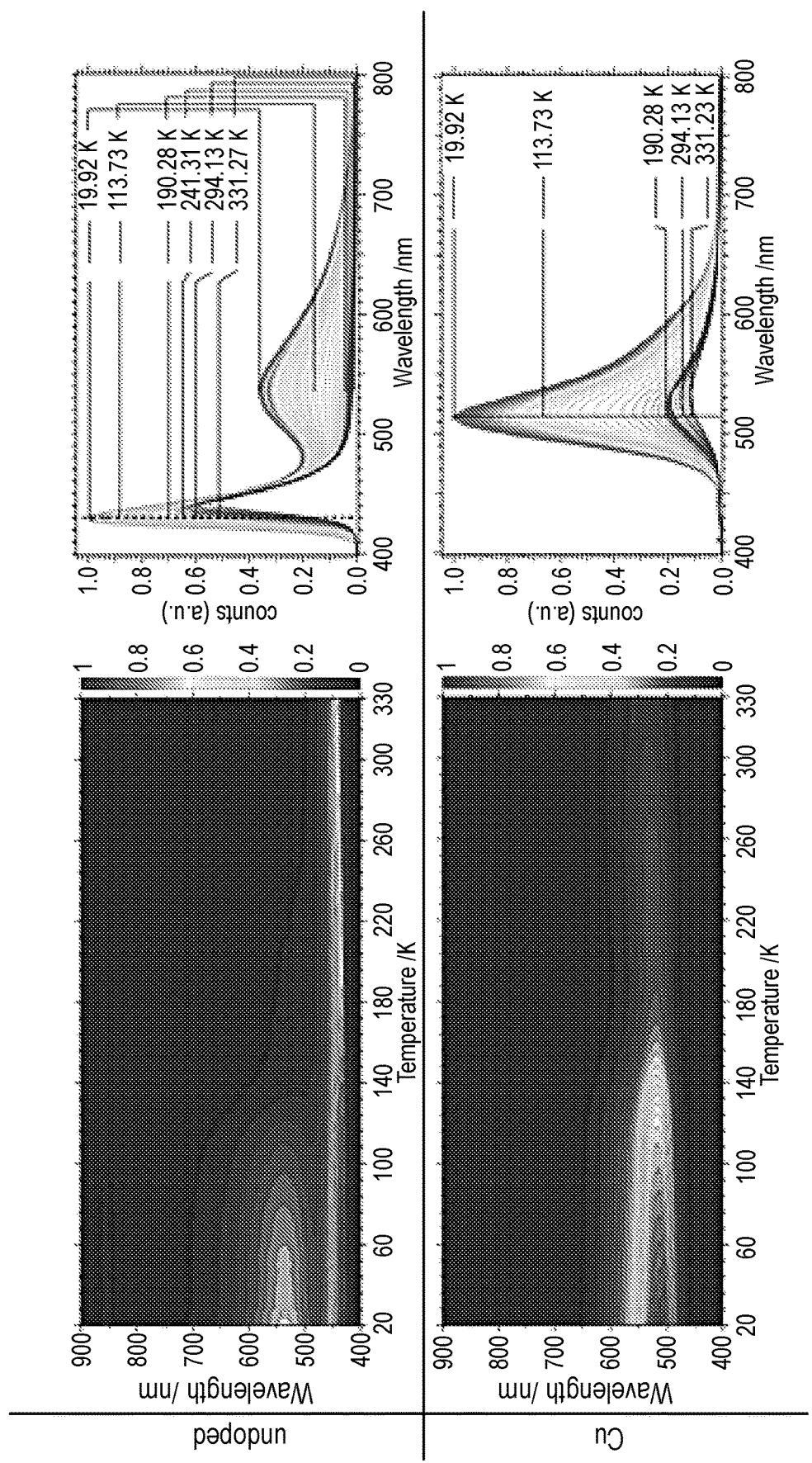
FIG. 15 depicts, in accordance with embodiments of the invention, temperature dependent PL of ZnSe/ZnS (undoped) (15A), ZnSe:Cu/ZnS (Cu) (15A), ZnSe:Cu,Al/ZnS (Cu,Al) (15B), ZnSe:Cu,Ga/ZnS (Cu,Ga) (15B), and ZnSe:Cu,In/ZnS (Cu,In) (15B) QDs. Excitation: 405 nm.
Figure 15B:
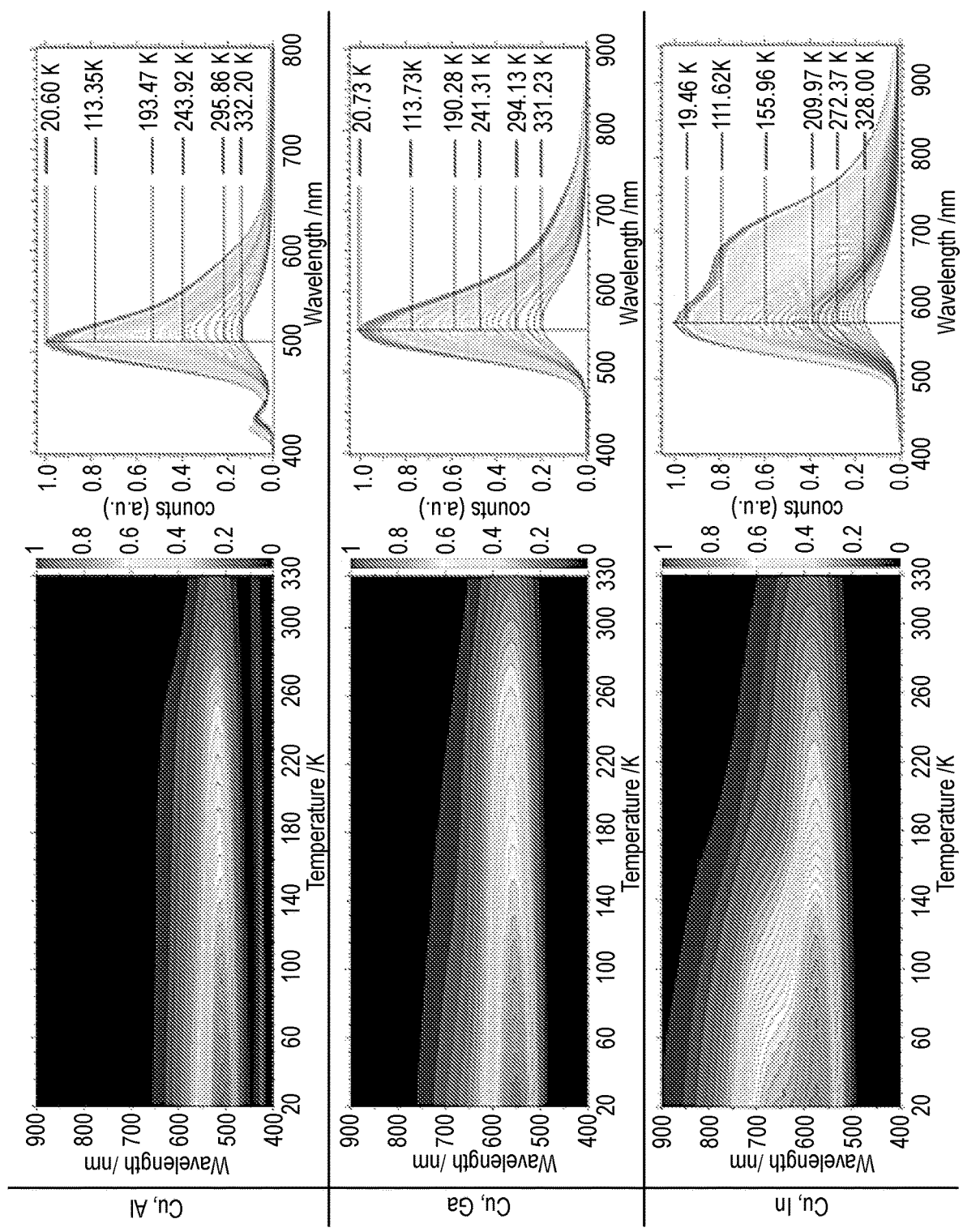

The effect of codoping on the PL of the QDs were examined through the temperature dependence of the PL from 18 to 330 K using a 405 nm (3.06 eV, $10^{-15}$ mW cm$^{-2}$) CW excitation light source. This temperature study reveals the existence of significant defect-related PL in the undoped, Cu-doped, and Cu,In-doped systems. The temperature dependence of the undoped ZnSe/ZnS QD PL is shown in FIG. 5(A) and those for the remaining samples are presented in FIG. 15. The primary defect emission is observed at 535 nm (2.32 eV) with a side band at approximately 650 nm (1.9 eV). The defect features decay monotonically with increasing temperature. The bandedge emission red shifts with increasing temperature, consistent with thermal activation of lattice phonons. The exact nature of the defect emission is beyond the scope of what is presented here. Here, it was used to qualitatively assess the quality of the QDs in terms of PL properties.

Figure 5B:
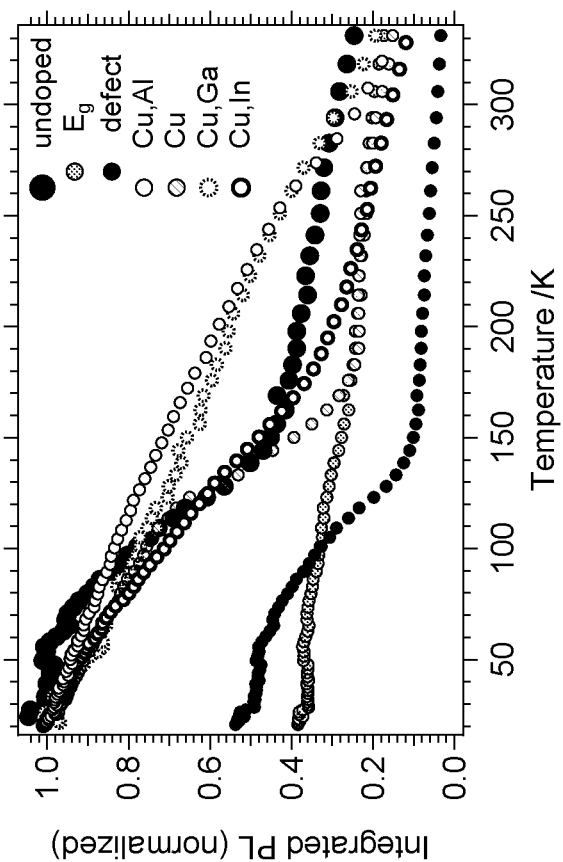
FIG. 5 depicts, in accordance with embodiments of the invention, (5A) temperature-dependent PL of the ZnSe/ZnS QDs with relative counts indicated by horizontal lines and labeled to relate to either band edge ($E_g$), or defect emission. Vertical line indicates the band edge emission position (429 nm) at 19.92 K. (5B) Temperature-dependent PL quenching of ZnSe/ZnS (undoped), ZnSe:Cu/ZnS (Cu), ZnSe:Cu,Al/ ZnS (Cu,Al), ZnSe:Cu,Ga/ZnS (Cu,Ga), and ZnSe:Cu,In/ ZnS (Cu,In) QDs. Also shown are the $E_g$ (400-490 nm) and defect (490-800 nm) integrated areas. Additional temperature-dependent spectra are shown in FIG. 15.
Figure 5A:
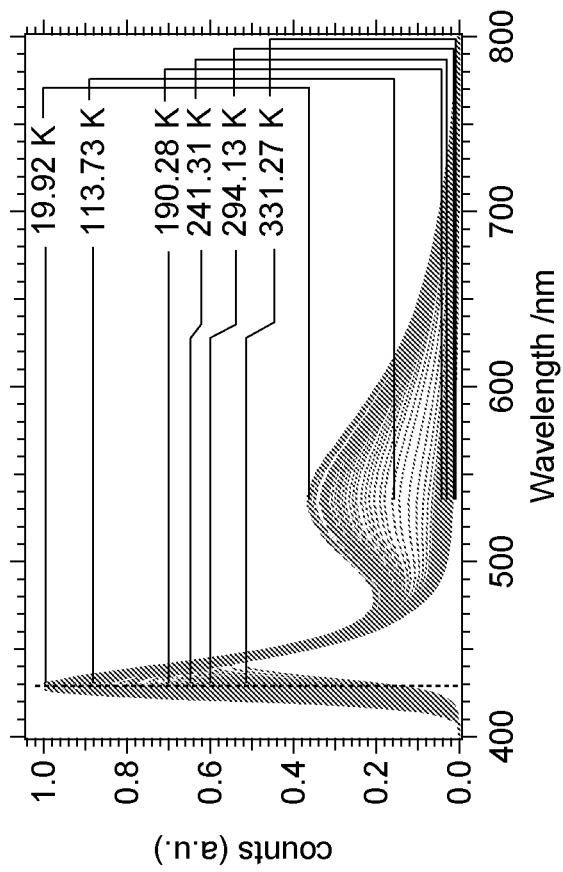
Figure 16:
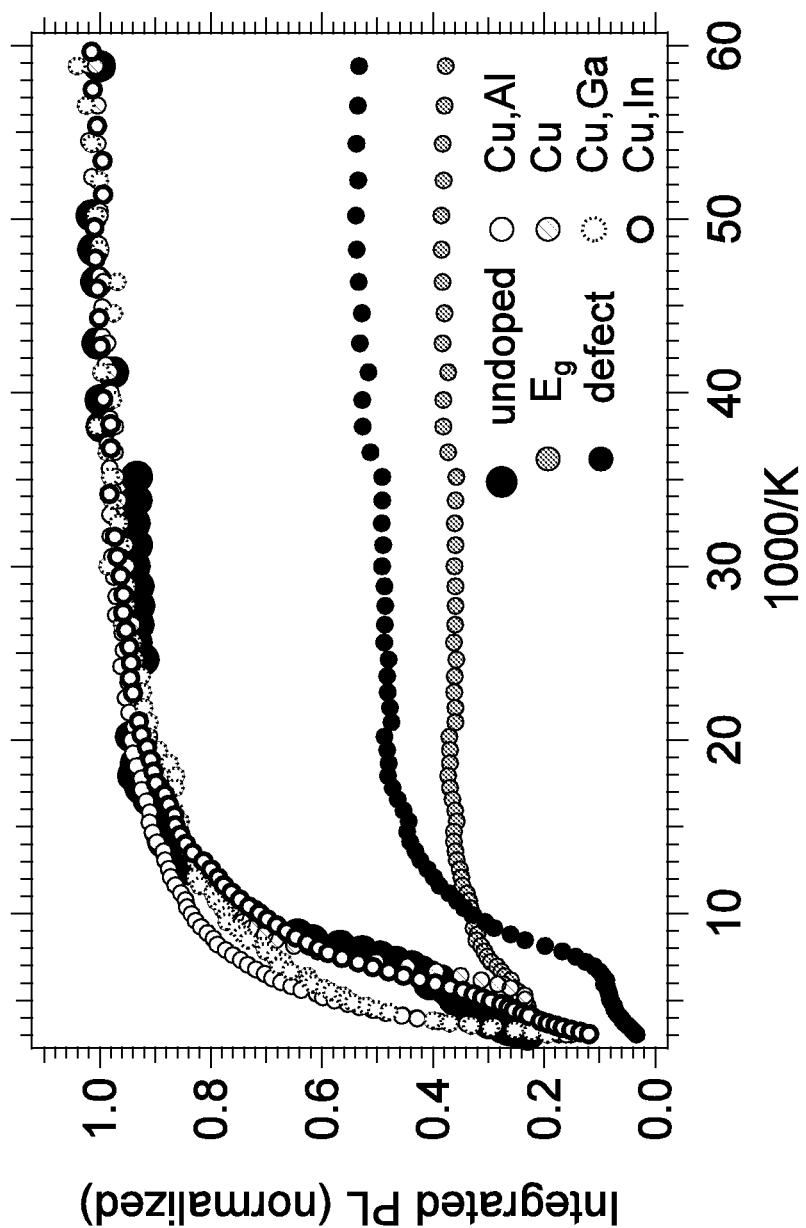
FIG. 16 depicts, in accordance with embodiments of the invention, temperature dependence of the integrated PL spectrum of ZnSe/ZnS (undoped), ZnSe:Cu/ZnS (Cu), ZnSe:Cu,Al/ZnS (Cu,Al), ZnSe:Cu,Ga/ZnS (Cu,Ga), and ZnSe:Cu,In/ZnS (Cu,In) QDs. Excitation: 405 nm.

The temperature dependence of the integrated PL spectrum for all five samples is shown in FIG. 5(B) and the Arrhenius plot is shown in FIG. 16. Additionally, for the undoped sample, the bandedge ($E_g$) and defect-related PL integrated from 400-475 nm and 475-800 nm, respectively, are also shown. Here, the defect-related PL exhibits a strong sigmoidal thermal quenching response between 70 and 160 K, whereas the bandedge PL has a more modest and linear dependence on temperature starting with a QY of 38% at 20 K and decreasing to 17% at 330 K. This effect is observed in the undoped, Cu-doped, and Cu,In codoped samples. However, the Cu,Al and Cu,Ga samples do not exhibit the same drop in integrated PL intensity in this temperature range. While not wishing to be bound by any one theory, the absence of these defect-related PL in the Cu,Al and Cu,Ga samples suggests that codoping with Al or Ga helps to eliminate intrinsic defect trapping/emission in Cu-doped ZnSe.

Measurements of the fluorescence quantum yield (QY) can be challenging due to a number of factors. Furthermore, considering the system under study is not a simple two level system, but rather involves multiple recombination pathways, the focus was on the external quantum efficiency (EQE). In an attempt to estimate the EQE of these QDs, two methods were employed to provide a lower and upper limit. The first method was through comparison of the PL intensity and optical density of the QDs to that of a perylene dye (with known QY=0.87, in ethanol). By this method, the QY of the samples were 10±5%. However, this method did not provide the precision necessary to discriminate between the samples.

Alternatively, an upper bound was placed on the EQE by considering the low temperature (18 K) PL intensity to have a unity EQE. At room temperature, the EQE is observed to be as follows: undoped (30%)=Cu,Ga (30%)>Cu,Al (25%)>Cu (20%)=Cu,In (20%). From this EQE perspective, the optimal codopant in this system is therefore $Ga^{3+}$, which is attributed to its ideal size compared to the host lattice and lack of defect formation as the $Ga^{3+}$ charge balances that of $Cu^+$. For the Cu doped sample, compensating $V_{Se}$ defect formation arises due to charge imbalance upon $Cu^+$ introduction. The local defect introduces additional non-radiative recombination pathways which decrease the EQE with respect to the other samples. Considering the Cu,In sample, increased lattice strain from the large In size relative to Al and Ga suggests that defects are introduced upon In codoping to accommodate lattice distortion. However and interestingly, the Cu,In sample has the longest lifetime of all the samples studied, vide infra, which implies that the square transition dipole moment ($|\mu_{if}|^2$) is highest in this sample. This should translate to increased EQE, however, defect emission present in this sample suggests that alternative pathways for recombination exist apart from the desired DAP ($In^{+2}+Cu^{+2} \rightarrow In^{+3}+Cu^{+}+h\nu$) channel that results in decreased EQE. While EQE is lower in this sample, the internal QY for this DAP channel is likely much higher actually, as suggested by the increased radiative lifetime compared to other samples studied. Hence, while EQE is useful for helping gain a better understanding of overall performance efficiencies, the internal QY for the DAP channel of interest is not well represented by these measurements. It is likely that Cu,In could be further optimized to eliminate these defect channels.

Increased Lifetime of Photocarriers with Codoping

Figure 6:
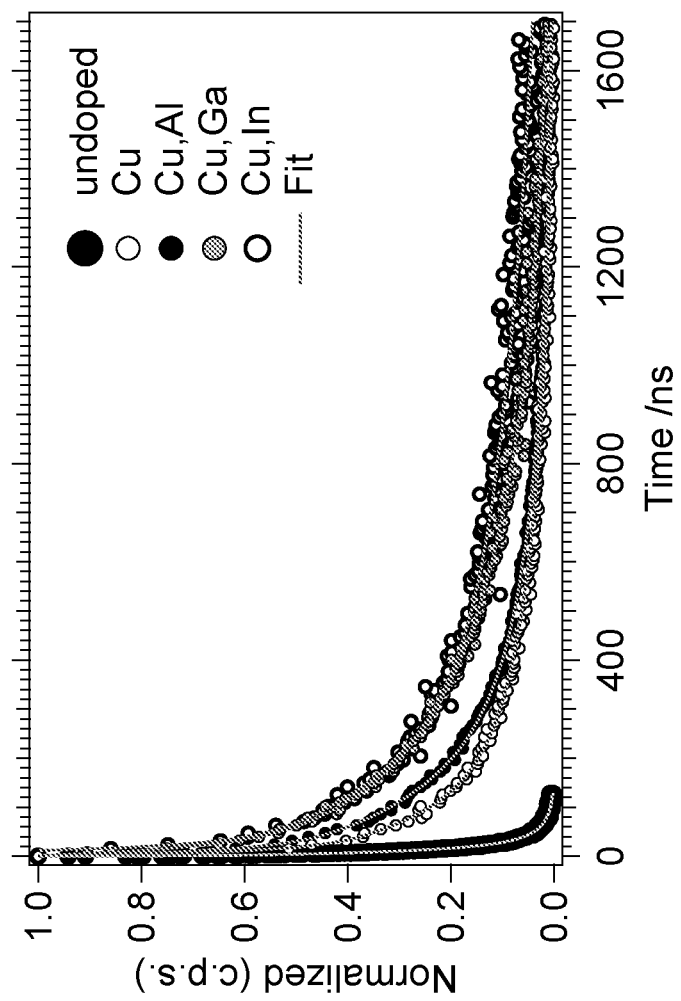
FIG. 6 depicts, in accordance with embodiments of the invention, time-resolved photoluminescence of undoped ZnSe/ZnS (undoped), ZnSe:Cu,Al/ZnS (Cu,Al), ZnSe:Cu/ ZnS (Cu), ZnSe:Cu,Ga/ZnS (Cu,Ga) and ZnSe:Cu,In/ZnS (Cu,In). Fit traces are shown superimposed. Spectra were fit with a triple exponential decay; extracted time constants and amplitudes are displayed in Table 1.

To further elucidate the effect of the dopant and codopants on the recombination pathways of photogenerated charge carriers in the ZnSe host lattice, the time dependence of the PL was investigated with time-correlated single photon counting (TCSPC) technique by monitoring the $\lambda_{max}$ for the Cu-related emission for the doped samples and the $\lambda_{max}$ for the band edge PL of the undoped sample, (FIG. 6). The undoped ZnSe/ZnS signal decayed completely within a hundred ns, a time frame typical of similar QD core/shell structures. In stark contrast, all the doped samples exhibited decays which extended for several hundreds of ns, which is also consistent with previous reports.

This result shows that introduction of the dopant significantly stabilizes the photogenerated carriers.

To extract the lifetimes and gain deeper insight into the fundamental recombination processes from the dynamics traces, a multi-exponential fitting procedure was applied to each trace using Equation 2 in which $\tau_i$ and $A_i$ are the fundamental time constant and initial amplitude of the $i^{th}$ recombination channel, respectively. All samples required a triple exponential fit and the resultant $\tau_i$ and $A_i$ values are listed in Table 1; the fits are also shown in FIG. 6.

$$I(t)=\Sigma_{i=1}^{3}A_i e^{-t/\tau_i} \qquad (2)$$

TABLE 1

Triple exponential fitting results of the single wavelength traces from the TCSPC measurements.

| | Amplitude | | | % Photon Flux | | | Lifetime/ns | | |
|---|---|---|---|---|---|---|---|---|---|
| | 1 | 2 | 3 | 1 | 2 | 3 | 1 | 2 | 3 |
| undoped | 0.260 | 0.535 | 0.204 | 2.19 | 45.1 | 53.9 | 0.93 | 9.3 | 30 |
| | (0.006) | (0.002) | (0.054) | (0.28) | (10.4) | (4.5) | (0.1) | (1.4) | (4.5) |
| Cu, Al | 0.409 | 0.360 | 0.231 | 2.00 | 25.9 | 72.1 | 7.5 | 110 | 476 |
| | (0.005) | (0.018) | (0.042) | (0.15) | (4.4) | (2.9) | (1.1) | (16) | (71) |
| Cu | 0.494 | 0.335 | 0.175 | 3.05 | 25.8 | 71.2 | 7.8 | 87 | 466 |
| | (0.005) | (0.019) | (0.034) | (0.23) | (4.4) | (2.4) | (1.2) | (13) | (70) |
| Cu, Ga | 0.408 | 0.343 | 0.275 | 2.54 | 20.8 | 77.4 | 16 | 156 | 714 |
| | (0.003) | (0.016) | (0.060) | (0.53) | (3.6) | (3.9) | (2.5) | (23) | (110) |
| Cu, In | 0.634 | 0.237 | 0.131 | 4.23 | 20.1 | 75.9 | 9.4 | 120 | 825 |
| | (0.003) | (0.017) | (0.021) | (0.85) | (3.2) | (1.2) | (1.4) | (18) | (120) |

Wavelengths selected are at the $\lambda_{max}$. Values and (errors) are reported for the initial amplitude, relative photon flux, and lifetimes (ns). Sample IDs describe: ZnSe/ZnS (undoped), singly-doped ZnSe:Cu/ZnS (Cu), and codoped ZnSe:Cu, Al/ZnS (Cu, Al), ZnSe:Cu, Ga/ZnS (Cu, Ga), and ZnSe:Cu:In/ZnS (Cu, In) QDs.

For undoped ZnSe, the fitting revealed three components with lifetimes of 0.9, 9.3, and 30 ns. The majority of the recombination occurred through the 9.3 ns pathway and is attributed to band edge recombination. The slow component (30 ns) is attributed to carrier trapping and the fast component (0.9 ns) dominated by non-radiative recombination channels. For the doped samples, the extracted lifetime components were on the order of fast (~10 ns), medium (~100-200 ns), and slow (~600-1000 ns) time scales. Any difference in the fast component of the doped samples was indistinguishable within the error of the measurements. However, the medium lifetime of the doped samples increased in order of Cu<Cu,Al≈Cu,In<Cu,Ga, and was found to be 87 ns±13, 110 ns±16, 120 ns±18, and 156 ns±23, respectively. Finally, the longest time constant increased in order of Cu=Cu,Al<Cu,Ga<Cu,In, and was found to be 470 ns±70, 480 ns±70, 710 ns±110, and 940 ns±150, respectively. The change in lifetime is attributed to stabilization of photocarriers at the $Cu^+$ and $D^{3+}$ states within the bandgap. From previous reports, Cu introduces an acceptor level at ~500-600 meV above the valence band (VB) edge due to the $t_2$ orbitals. Upon excitation of the host lattice, the photogenerated hole will become trapped at this acceptor level, transforming $Cu^+$ into $Cu^{2+}$ in the excited state and giving it the same oxidation state as the host lattice ($Zn^{2-}$). This $d^9$ species has the beneficial effect of stabilizing the photohole, thereby increasing the PL lifetime in the singly-doped ZnSe system.

Upon introduction of $Al^{3+}$, the increase in the medium lifetime component is attributed to elimination of $V_{Se}^{-2}$ defects. From the PL studies, $Al^{3+}$ does not result in a red shift of the Cu-related PL, indicating it does not introduce an acceptor level below the CBM, similar to the case observed in CdS QDs. Additional stabilization of the excited state species was observed for the case of $Ga^{3+}$ and $In^{3+}$ codopants, evidenced by the increase in the slow time constant for these samples. As both codopants have the effect of redshifting the PL, it is inferred that Ga and In introduce donor levels in the bandgap of the host that act to localize and trap the photoelectron thereby forming either $Ga^{2+}$ or $In^{2+}$ in the excited state. The combined effect of photohole and photoelectron stabilization in the Cu,Ga and Cu,In doped systems increases the PL lifetime significantly over the Cu and Cu,Al samples. For the Cu; Cu,Ga; and Cu,In codoped QDs, it was concluded that the PL is generated through donor acceptor pair (DAP) recombination of the excited carriers.

Local Structure of the Primary Dopant

To gain further understanding of the effect of codoping on the electronic structure of the QDs, the local lattice structure of the dopant sites was next studied. To accomplish this goal, extended X-ray absorption fine structure (EXAFS) was employed as it allows bond distances to be measured at resolutions of 0.1 Å with an accuracy of 0.02 Å with elemental specificity.

Figure 7B:
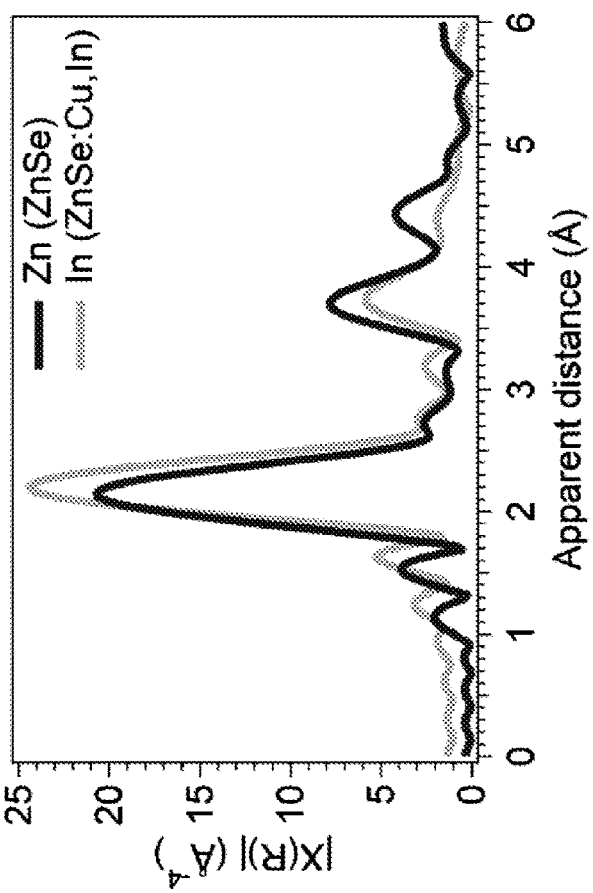
Figure 7A:
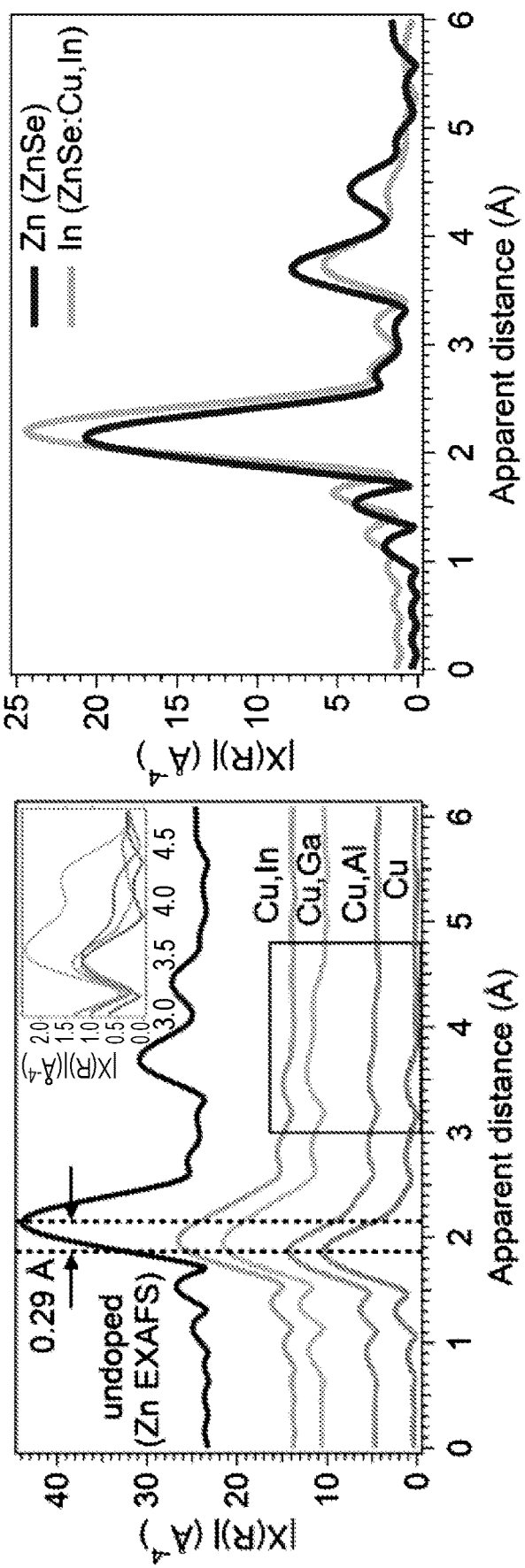

The Fourier transformed spectra for the Cu and Zn EXAFS of all samples are shown in FIG. 7A. The peaks in the spectrum indicate the average distances of atoms adjacent to the element of interest, as observed up to three neighbors away. Note that a well-known photoelectron phase shift moves the apparent peak positions to a distance ~0.40 Å shorter than the expected value, and the actual distances can be obtained via fitting of the EXAFS data. The relative amplitudes offer information regarding the number of neighboring atoms in each shell and are also strongly coupled with the crystallinity/distance distribution of the local structure surrounding the absorbing atom.

Figure 17A:
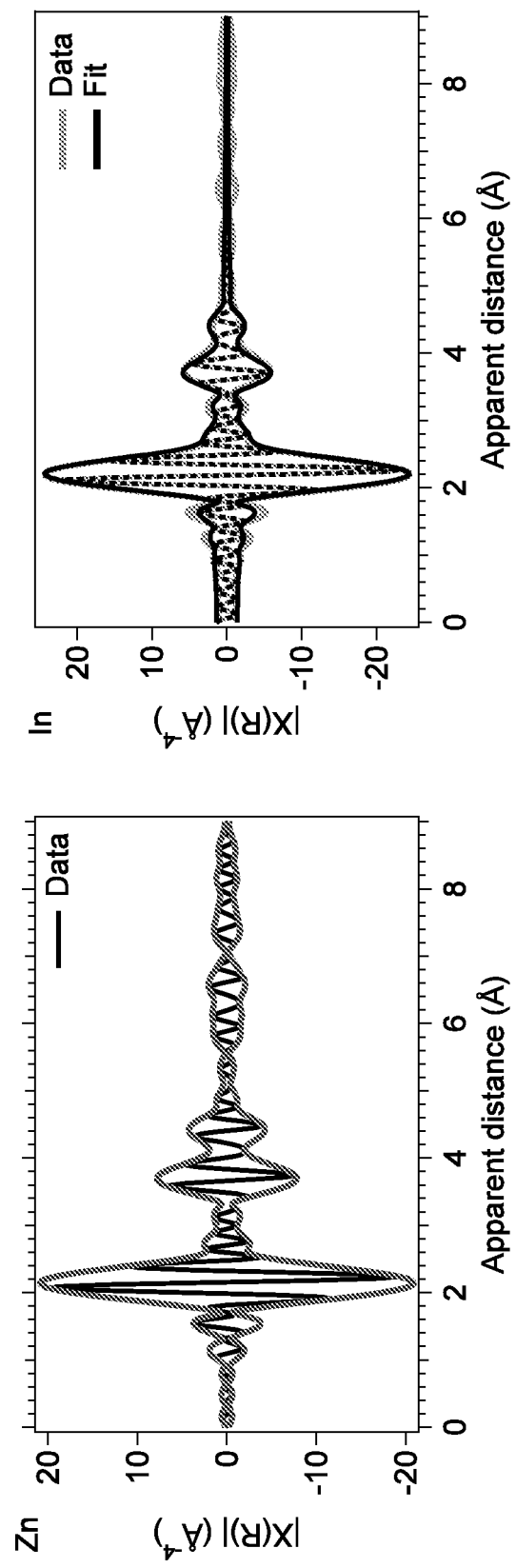
FIG. 17 depicts, in accordance with embodiments of the invention, EXAFS data for Zn from ZnSe QDs (17A) as well as data and fits for In EXAFS from ZnSe:Cu,In/ZnS (Cu,In) QDs (17A) and Cu EXAFS from ZnSe:Cu/ZnS (Cu) (17B), ZnSe:Cu,Al/ZnS (Cu,Al) (17B), ZnSe:Cu,Ga/ZnS (Cu,Ga) (17C), and ZnSe:Cu,In/ZnS (Cu,In) (17C) QDs.
Figure 17B:
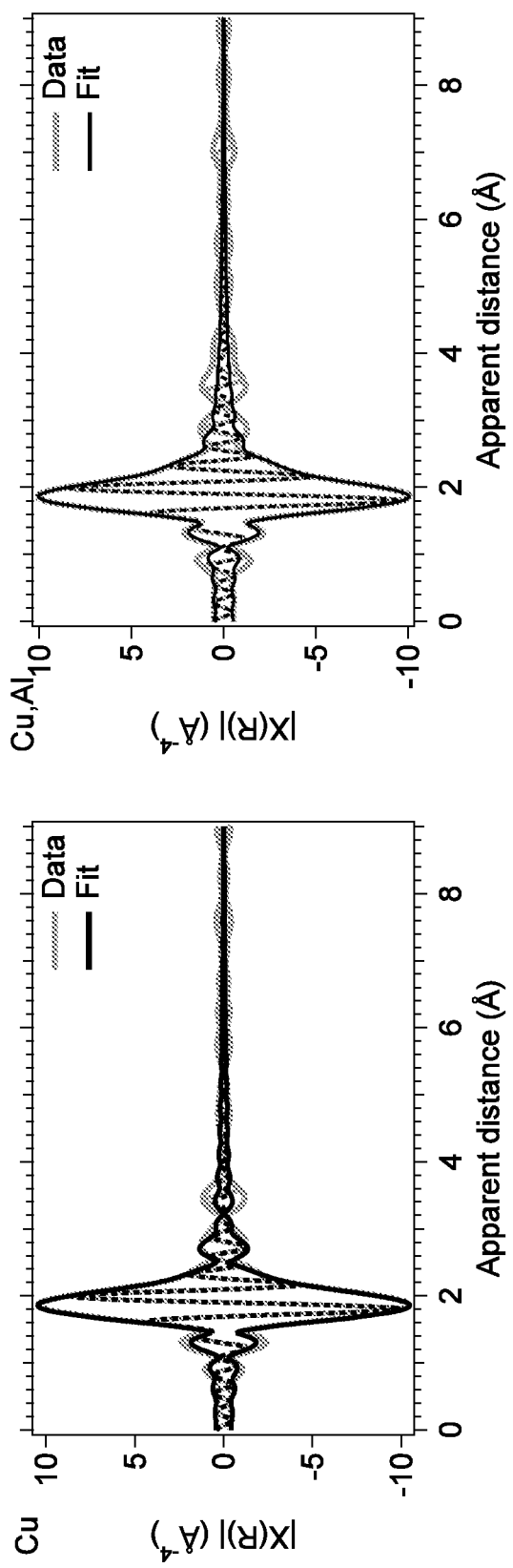
Figure 17C:
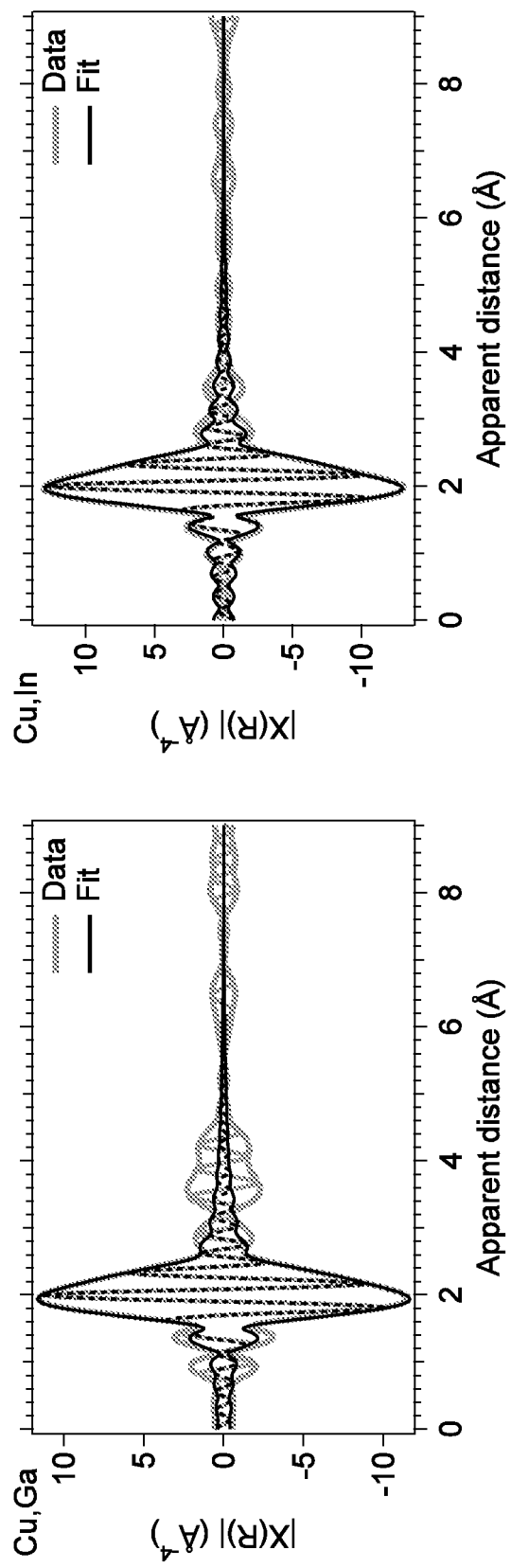

Theoretical EXAFS parameters were calculated starting with cubic ZnSe and replacing the central Zn with Cu. However, in all samples, a Cu—S path has to be included to fit the data, which indicates that some of the Cu is either present on the surface of the ZnSe core or enters the ZnS shell. The latter case is not an unreasonable conclusion considering the synthesis was performed in one pot and residual Cu in the crude pot is likely. The best fits obtained for the first shell using a two phase system are shown in FIG. 17 along with the data. The fit results are presented in Table 2. As more than one phase existed, leading to multiple shell contributions, a variable parameter x was introduced into the EXAFS equation used by the Artemis program of the IFEFFIT package, shown in Equation 3, where $x_i$ is the individual contribution of each phase and $X_i(k)$ is the EXAFS function of each individual phase.

$$X_{total}(k) = \Sigma_i x_i X_i(k) \qquad (3)$$

TABLE 2

Local structure parameters for In and Cu in the various QD samples as determined from the best fits of Fourier transformed data.

| Sample | Path | R (Å) | N | $\sigma^2$ (Å$^2$) | x (%) | R-factor | $\chi^2_{red}$ |
|---|---|---|---|---|---|---|---|
| ZnSe Bulk | Zn—Se | 2.45 | 4 | | | | |
| | Zn—Zn | 4.01 | 12 | | | | |
| | Zn—Se | 4.70 | 12 | | | | |
| ZnSe:Cu, In | In—Se1 | 2.55 ± 0.003 | 4.0 ± 0.3 | 0.002 ± 0.0003 | | 0.003 | 18 |
| (In EXAFS) | In—Zn | 4.03 ± 0.02 | 9.3 ± 0.4 | 0.007 ± 0.002 | | | |
| | In—Se2 | 4.66 ± 0.01 | 7.9 ± 0.4 | 0.009 ± 0.005 | | | |
| ZnSe:Cu | Cu—Se | 2.35 ± 0.01 | 3 | 0.009 ± 0.004 | 34 | 0.0002 | 405 |
| | Cu—S | 2.25 ± 0.01 | 3 | 0.002 ± 0.001 | 66 | | |
| ZnSe:Cu, Al | Cu—Se | 2.37 ± 0.02 | 4 | 0.017 ± 0.003 | 51 | 0.0007 | 474 |
| | Cu—S | 2.25 ± 0.01 | 4 | 0.001 ± 0.0008 | 49 | | |
| ZnSe:Cu, Ga | Cu—Se | 2.39 ± 0.01 | 4 | 0.007 ± 0.001 | 60 | 0.0006 | 351 |
| | Cu—S | 2.27 ± 0.01 | 4 | 0.006 ± 0.002 | 40 | | |
| ZnSe:Cu, In | Cu—Se | 2.38 ± 0.01 | 4 | 0.003 ± 0.001 | 53 | 0.0007 | 167 |
| | Cu—S | 2.27 ± 0.01 | 4 | 0.007 ± 0.002 | 47 | | |

Debye-Waller factor ($\sigma^2$) was used as a variable parameter whereas $S_0^2$ value was fixed to 0.83 for Cu and 0.94 for In data. Experimental structural parameters for bulk ZnSe (Wyckoff, R. W. G. *Crystal Structures* 2nd edn, Vol. 1 (Wiley, 1963) have also been listed. A k-space range of 2.5 < k (Å$^{-1}$) > 14 was used for In EXAFS, whereas a k-space window of 2.5 < k (Å$^{-1}$) > 11.5 was used for Cu EXAFS data.

Since the roles of $x_i$ and the coordination number (Nj) should be complementary, the coordination number for each phase was fixed while x was used as a variable parameter during the fitting process.

From the EXAFS data fitting and analysis, it is estimated that only ~30% of the $Cu^+$ in the Cu sample has Se nearest neighbors, whereas the remaining Cu has S neighbors. The addition of $Al^{3+}$ as a codopant increased the fraction of $Cu^+$ associated with the ZnSe core to ~50% while addition of $Ga^{3+}$ improved the $Cu^+$ doping to ~60%. The core content was comparable for Cu,In and Cu,Al codoping. The inclusion of $D^{3+}$, also at a $Zn^{2+}$ site, allows for the addition of a $Cu^+$ atom without creating a selenium vacancy ($V_{Se}^2$), thereby increasing the solubility in the core. Local structure parameters for In and Cu in the QD samples as determined from the best fits of Fourier transformed data are given in Table 2.

In cubic, undoped ZnSe, Zn is tetrahedrally coordinated by 4 Se atoms which are at a distance of 2.45 Å, and the corresponding peak in the EXAFS data appears at an apparent distance of ~2.1 Å. The second peak at 3.65 Å and third peak at 4.40 Å originate from the 12 Zn second neighbors and 12 Se third neighbors, which are at distances of 4.01 and 4.70 Å, respectively. In the Cu sample, the average Cu—Se distance is 2.35 Å, which is 0.1 Å shorter than the Zn—Se bond length (FIG. 7A). A lengthening of the Cu—Se bond distance to 2.37 Å was observed in Cu,Al. This suggests that the environment around Cu is less distorted as compared to the sample without the codopant by elimination of $V_{Se}^{2-}$ and return of Cu toward a tetrahedral-like geometry. For Cu,Ga, the Cu—Se distance was found to be 2.39 Å, which again is closer to that of a perfect tetrahedral site (2.45 Å). This effect is attributed to smaller lattice distortions due to comparable sizes of Zn, Cu, and Ga. Finally, in Cu,In, the Cu—Se distance was 2.38 Å as a result of the larger In size leading to increased lattice strain.

Further evidence of the change in local structure symmetry can be found from examination of the second and third neighbor amplitudes. For the Cu trace (FIG. 7A), the second and third neighbor peaks are absent, whereas for Cu,Al, the second and third neighbor peaks increase in amplitude (more easily seen in the inset of FIG. 7A). Likewise, Cu,Ga exhibits an additional increase in these two peaks. On the other hand, the second and third neighbor peaks decrease in amplitude for Cu,In. These results suggest that the size of the codopant strongly affects the degree of disorder around the primary dopant. As previously discussed, doping with only $Cu^+$ results in a lattice charge imbalance which may be compensated through doping with a second $Cu^+$ and creating a Se vacancy (VSe). Considering the second and third neighbor amplitudes, it is evident that the $V_{Se}^{2-}$ is created adjacent to the Cu dopants. Ga is comparable in size to that of Zn and Cu and thus results in the least disorder around the primary dopant. Furthermore, the effect of the codopant on the local structure of Cu suggests that the codopant occupies a lattice site in the vicinity of the $Cu^+$ dopant. Consequently, the DAP-related recombination described previously occurs through a spatially localized photohole and photoelectron at the acceptor and donor sites.

Local Structure of the Codopant

EXAFS studies of the $Al^{3+}$ codopant are hampered by Se $L_1$-edge absorption overlap, and in the case of $Ga^{3+}$, overwhelming fluorescence signal from Zn makes it impossible to measure the absorption spectrum using fluorescence yield. Consequently, $In^{3+}$ was the only viable option for studying local structure of the codopant. The EXAFS signal for In is shown in FIG. 7B, along with that of $Zn^{2+}$ for comparison. High similarity between the In and Zn EXAFS indicates that $In^{3+}$ occupies a $Zn^{2+}$ substitutional site. However, the first peak for $In^{3+}$ appears at a slightly longer distance as compared to $Zn^{2+}$. From EXAFS fitting analysis, the In—Se first neighbor distance was longer than that of Zn—Se by 0.10 Å, extending to 2.55 Å instead of 2.45 Å (Table 2). The Se atoms are pushed to longer bond distances because of the larger ionic size of $In^{3+}$ compared to $Zn^{2+}$.

Density Function Theory Calculations of $Cu^+$ Doped and $D^{3+}$ Codoped ZnSe

To further understand the origin of the PL in the codoped ZnSe system as a consequence of doping and codoping, density functional theory (DFT) was applied to a 64 atom ZnSe super cell as a model system. The cubic super cell was optimized to obtain a unit cell parameter of a=5.67 Å. In this unit cell, one Zn was replaced with Cu and the bond distances from Cu to three of the nearest Se atoms was fixed to the bond distance determined with EXAFS (Cu–Se=2.36 Å). A second Zn directly adjacent to the Cu was replaced by the D atom (D=Al, Ga, In, or Tl) in the case of the donor systems. For the ZnSe:Cu system, a second Zn was replaced by a Cu and the shared Se atom was removed to create the $V_{Se}^{-2}$ necessary for charge neutrality. Compared to a previous report (See Gul, S.; Cooper, J. K.; Glans, P.-A.; Guo, J.; Yachandra, V. K.; Yano, J.; Zhang, J. Z. Effect of Al3+ co-doping on the dopant local structure, optical properties, and exciton dynamics in Cu+-doped ZnSe nanocrystals. ACS Nano 2013, 7, 8680-8692.) all lattice ion positions were optimized with the exception of the constraint on the Cu—Se bond distance; DFT modeling was not able to correctly predict the defective Cu—Se bond distance in the ZnSe lattice, which EXAFS reveals is defect trigonal planar, as by geometry optimization of the Cu local structure results in a perfect tetrahedral local structure. The codopant however, as was previously discussed, is tetrahedral in the ZnSe:Cu,In system and therefore by extension should also be tetrahedral for the other codopants. The bond distances to nearest neighbors vary as a consequence of the ion size being different as compared to Zn. The optimized D-Se bond distances were 2.456 Å (Al—Se), 2.481 Å (Ga—Se), and 2.642 Å (In—Se) while the host bond distance was 2.454 Å (Zn—Se).

Figure 8:
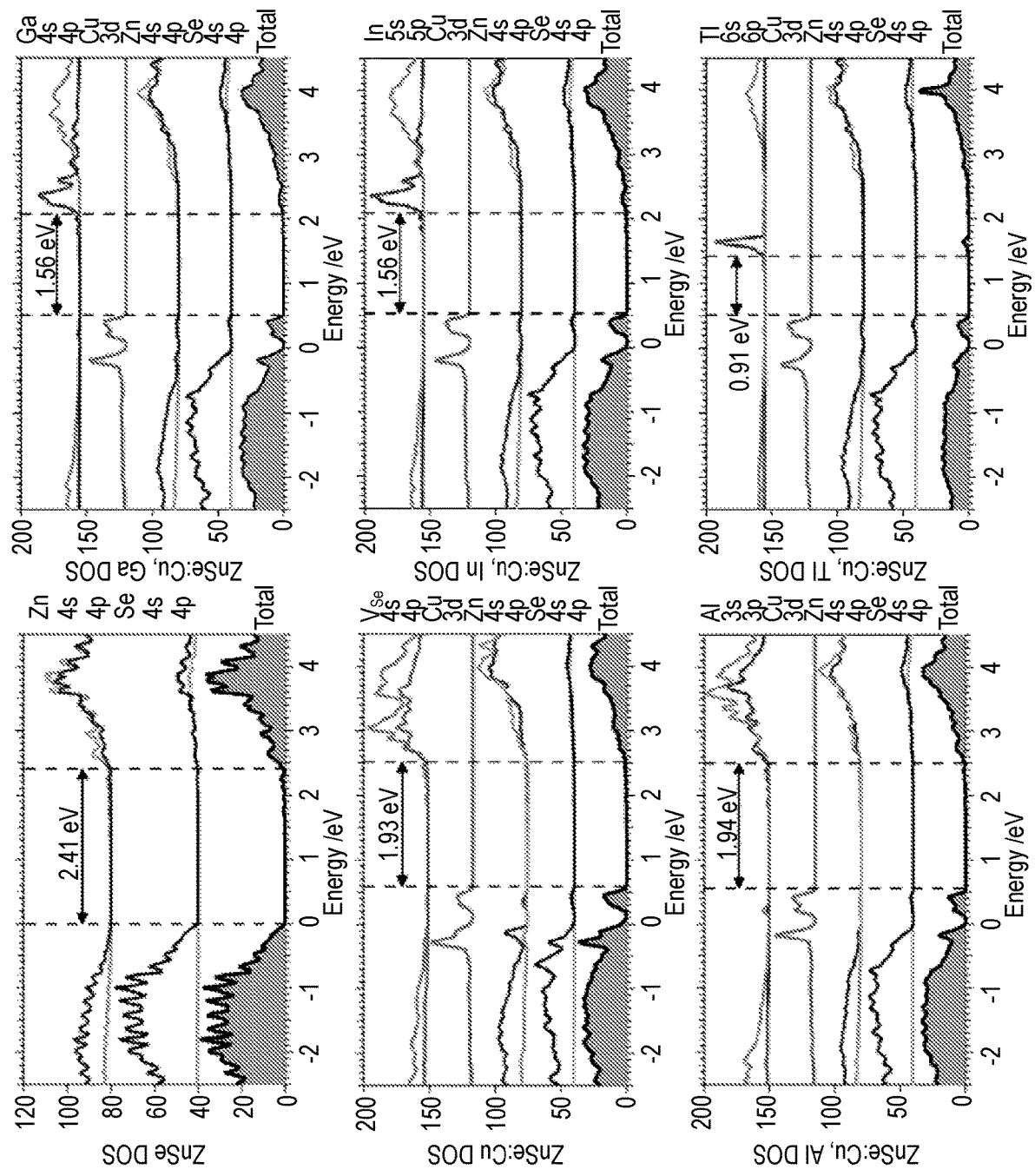
FIG. 8 demonstrates, in accordance with embodiments of the invention, DFT calculations of the PDOS for ZnSe:$Cu^+$, $D^{3+}$ (D=Al, Ga, In, Tl).

The partial density of states (PDOS) for all the systems under investigation were reported in FIG. 8. For the host ZnSe system, the predicted Eg was 2.41 eV which is a factor of 0.89 lower than the expected $E_g$ of 2.70 eV. From the PDOS, the valence band (VB) is primarily Se 2p character hybridized with Zn 4p. The conduction band (CB) is a mixture of both Zn 4p and 4s as a result of sp3 hybridization in the tetrahedral ligand field. These states are also well hybridized with Se 2p in the CB.

Doping with Cu introduces two new states, the ligand field split d orbitals forming the e and $t_2$ levels. The Cu e states are located within the VB and contribute to the VBM while the $t_2$ states are observed between 0.16 and 0.56 eV above the VBM. The defective Zn, adjacent to the $V_{Se}^{-2}$ and having only three Se bonds, is indicated in FIG. 8 as 'VSe. The Zn 4p and 4s orbitals have significantly more DOS toward the CBM compared to bulk Zn and slightly extend into the band gap. This is contrary to a previous report where it was observed $V_{Se}$ states within the $E_g$. (See Gul, S.; Cooper, J. K.; Glans, P.-A.; Guo, J.; Yachandra, V. K.; Yano, J.; Zhang, J. Z. Effect of Al3+ co-doping on the dopant local structure, optical properties, and exciton dynamics in Cu+-doped ZnSe nanocrystals. ACS Nano 2013, 7, 8680-8692.). These states were removed upon improvements to the computational model by optimizing the local structure around the defect. From the combination of the two results it can be concluded that any deviation from the optimum structure will create additional states within the Eg related to the Zn dangling bonds. These states may become activated by phonons at elevated temperatures or lattice strain. The effects are not taken into account herein but are likely to play a significant role in the $V_{Se}$-related emission discussed above and in a previous report. Finally, the calculated gap related to Cu emission was 1.93 eV.

Doping with both Cu and Al introduces additional DOS from the Al 3s and 3p states. The Al-related states are well-hybridized with the CB and do not extend below the CBM. The 3s states do contribute to more DOS at the CBM relative to the 3p states, as was also the case for Zn. Consequently the $E_g$ was calculated to be 1.94 eV. This result is consistent with the observed PL shift between the Cu and Cu,Al samples where the Cu,Al was blue shifted of the Cu-only sample.

A significant change in the DOS was observed in ZnSe:Cu,Ga as a consequence of Ga. While the Cu states were the same as previously described ($t_2$=0.06 to 0.50 eV above the VBM), a new acceptor state related to Ga 4s was added at CBM−0.52 eV. The resulting gap between the Cu and Ga states was calculated to be 1.56 eV. The remaining Ga 4p states remained well-hybridized with the host lattice and mirrored the DOS seen from Zn 4p. This result supports the previously discussed model for DAP emission in this system.

Figure 9B:
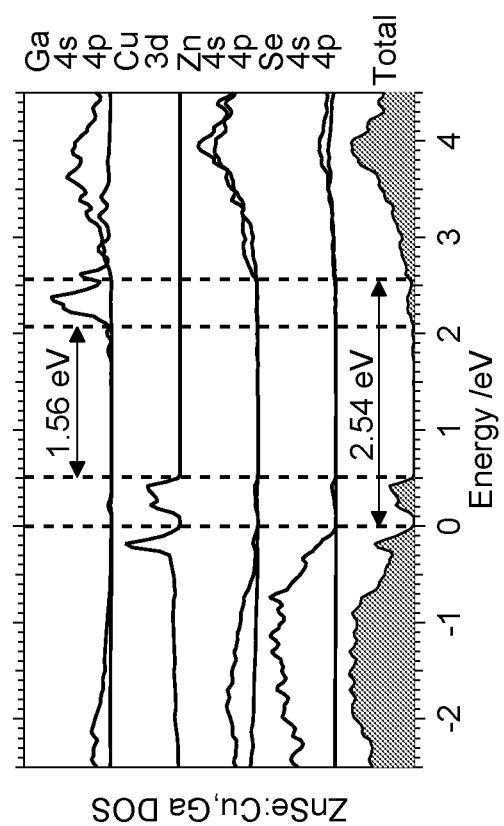
FIG. 9 demonstrates, in accordance with embodiments of the invention, (9A) density of states of ZnSe:Cu,Ga QDs in which both Cu and Ga are in perfect tetrahedral sites whereas (9B) has Cu in the distorted tetrahedral site, as expected from the EXAFS analysis.
Figure 9A:
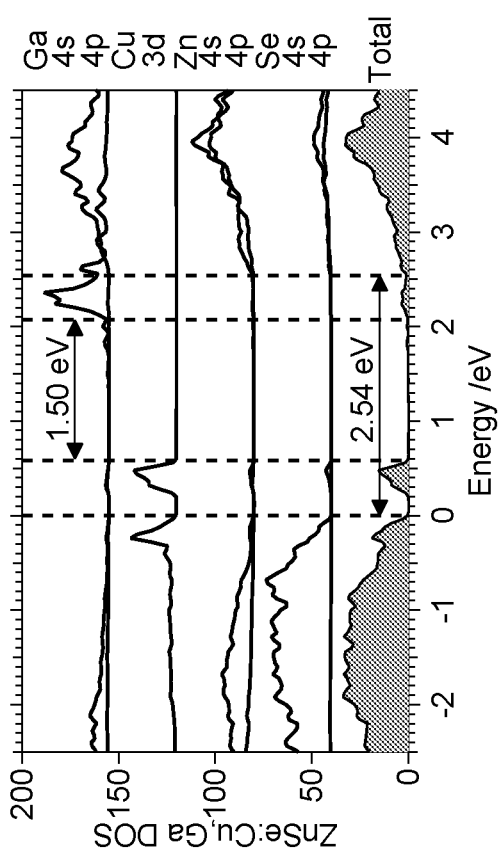

A similar effect was seen in the ZnSe:Cu,In sample, however the predicted bandgap is the same as that of ZnSe:Cu,Ga. This could arise from an inaccurate description of In in the computational model or because the Cu—Se bond distances were held constant during the optimization procedure for these calculations. The acceptor level of Cu is seen to change its energetic level depending on the magnitude of distortion away from perfect tetrahedral. The DOS for ZnSe:Cu,Ga in which the Cu—Se bond distances were not fixed during the optimization is shown in FIG. 9. This results in a perfect tetrahedral symmetry for Cu. Consequently, the predicted $E_g$ moved to 1.50 eV for the perfect tetrahedron (longer Cu—Se bond distances) from 1.56 eV with Cu in the distorted site (shorter Cu—Se bond distances). The red shift in the ZnSe:Cu,In PL, as compared to that of ZnSe:Cu,Ga, is likely a contribution from the slight change in the Cu local structure toward a more tetrahedral structure in the Cu,In system, which is consistent with the EXAFS analysis.

Figure 14:
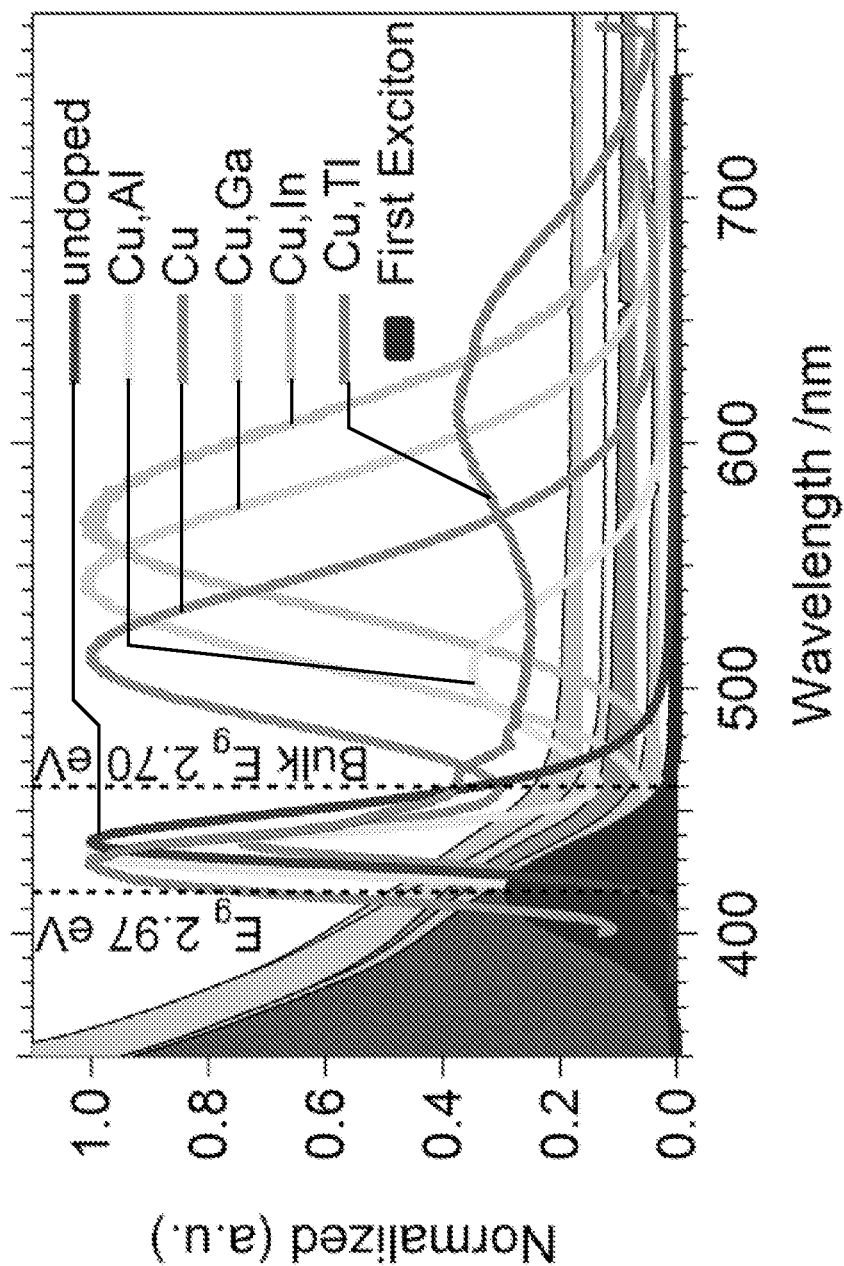
FIG. 14 depicts, in accordance with embodiments of the invention, normalized absorption and PL spectra ($\lambda_{ex}$=380 nm) of undoped ZnSe/ZnS (undoped), ZnSe:Cu,Al/ZnS (Cu,Al), ZnSe:Cu/ZnS (Cu), ZnSe:Cu,Ga/ZnS (Cu,Ga), ZnSe:Cu,In/ZnS (Cu,In), as well as ZnSe:Cu,Tl (Cu,Tl) QDs. Absorption spectra are shown as filled curves and PL spectra are shown as solid lines. Absorption spectra are offset for clarity. $E_g$ and Bulk $E_g$ represent the absorption onset of the ZnSe/ZnS QDs and bandgap of bulk ZnSe, respectively.

Finally, ZnSe:Cu,Tl (Cu,Tl) was studied as a potential candidate for red emission in this system. While attempts were made to produce the Cu,Tl variant, the large size of Tl is particularly challenging to incorporate and contributed to significant distortion to the host lattice. The PL of an example Cu,Tl sample is shown in FIG. 14 which demonstrates an emission maximum at approximately 635 nm. The significant host emission is indicative of incomplete doping and the significant broadening and multiple component emission in the red suggests inhomogeneous $Tl^{3+}$-related electronic states. When the ZnSe:Cu,Tl core was modeled, the PDOS related to Cu remained the same as previously described, however the donor state from Tl 6s moved to CBM−1.2 eV and extended up to CBM−0.84 eV. The resulting DAP recombination in this system is calculated to be 0.91 eV. For Tl→VBM 4s emission, the calculated transition would be 1.4 eV.

Energetic Model of $Cu^+$ Doped and $D^{3+}$ Codoped ZnSe

Figure 10A:
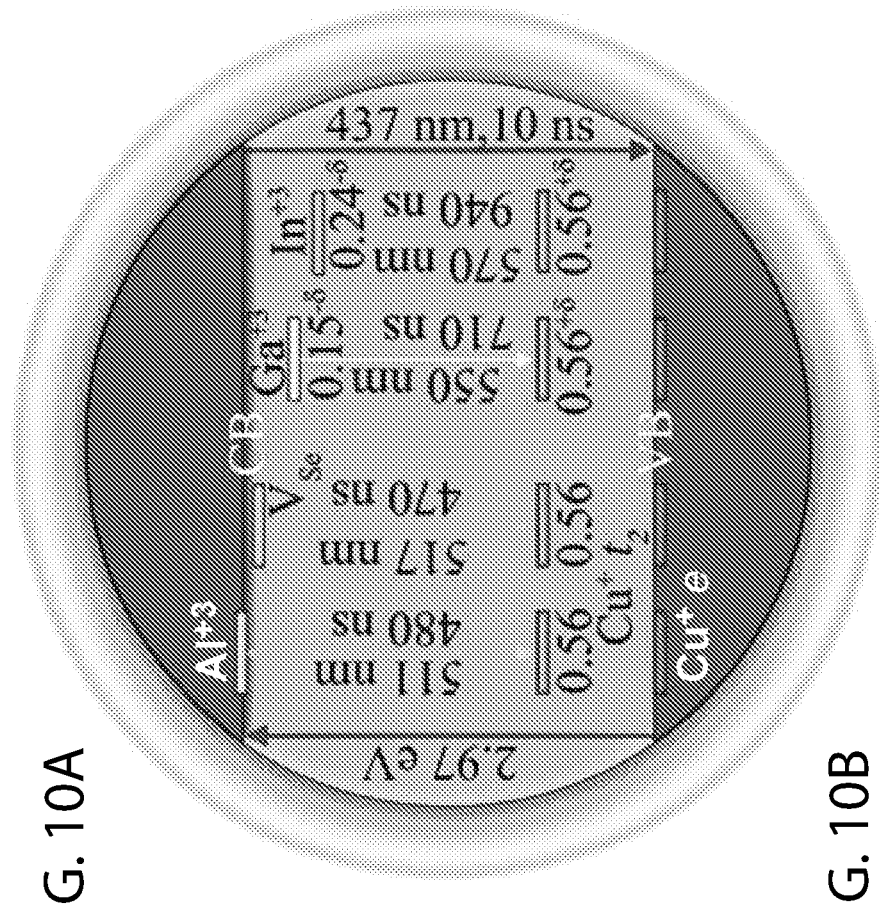
FIG. 10 depicts, in accordance with an embodiment of the invention, (10A) summary of the electronic energy levels and fluorescence lifetimes of ZnSe doped with $Cu^+$ and codoped with $Al^{+3}$, $Ga^{+3}$, or $In^{+3}$. (10B) Integrated local DOS showing the spatial occupation of the DOS for the VBM, Cu-related acceptor state, Ga-related donor state, and the CBM.

The energy levels of the donor and acceptor states described above, as well as the lifetimes for the various recombination channels, are summarized in the energy level model shown in FIG. 10A. The observed bandgap from UV-Vis is indicated (2.97 eV) as well as the band edge PL (437 nm). The energy levels of the dopant and codopants are provided with respect to either the VB or CB, respectively. The ±δ shown in FIG. 10A accounts for variation of the Cu level as a function of local structure distortions caused by the codopant, as previously discussed. The extent of tunability of these systems by quantum confinement has not been fully examined at this point, however, the Cu related emission in Cu:ZnSe has proven to be tunable through quantum confinement of the host allowing for an additional parameter to modify the emission.

Figure 10B:
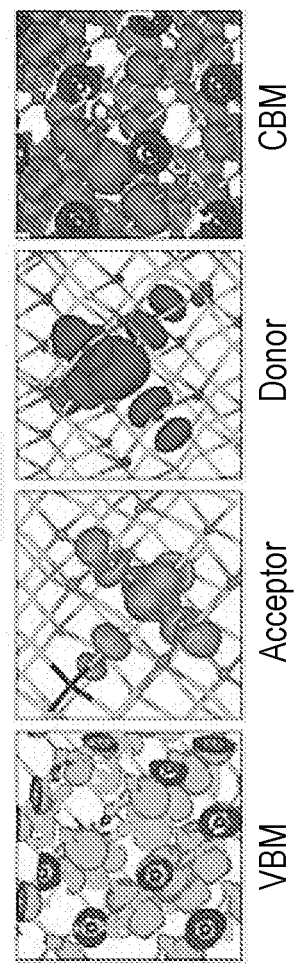

As a visualization aid for the states of interest, the integrated local DOS for the VBM, CBM, Cu-related acceptor, and dopant donor level for Ga (the In ILDOS are very similar to the Ga orbital shape) are shown in FIG. 10B. Here it is easy to see the spatial extent of charge localization on the donor and acceptor states, thereby improving the initial and final state wave function overlap that is critical for efficient PL with high yield.

Conclusion

As described herein, novel codoped, ligand-capped, core/shell ZnSe/ZnS QDs with PL tunable from blue to orange were synthesized and their morphological, optical, dynamic, and structural properties were characterized in detail. In single doping, Cu dopes the ZnSe lattice as a +1 ion at a Zn site, resulting in a lattice charge imbalance that is compensated for by the formation of Se vacancies. Utilization of a trivalent cation ($D^{3+}$) as a codopant reduces defect formation by neutralizing the charge imbalance from the initial Cu+ doping and consequently improves the PL EQE. The codopant also introduces a donor state into the ZnSe bandgap, whose energy level can be lowered further from the CB by changing the codopant from Al to Ga and In. The combination of these effects allows for tunable emission from ZnSe QDs throughout the visible region of the spectrum. The introduction of Cu has the effect of increasing the photohole lifetime compared to the undoped system, whereas Ga and In codopants stabilize the photoelectron lifetime, by localizing the carriers in mid-gap states. In addition, through incorporation of a ZnS shell in conjunction with a modified lipoic acid capping ligand, QD stability to post-synthetic processing and long term storage was substantially improved, and PL was enhanced by about one order of magnitude. Furthermore, EXAFS analysis elucidated the local structure of both the primary $Cu^+$ dopant and In codopant, indicating that they occupy a distorted trigonal planar and tetrahedral substitutional Zn site, respectively. The dopant and codopants were seen to occupy neighboring lattice positions which results in increased wave function overlap for improved PL emission. Computational studies provide further insight into the electronic states involved and their related energy levels as well as correlation to structural properties. The codoped ZnSe/ZnS QD system described herein represents an efficient and economical alternative to conventional CdSe lighting materials, and should reduce the use of toxic Cd while still offering improved chromophoric quality of display devices through tunable emission with limited self-absorption.

Methods

ZnSe/ZnS, ZnSe:Cu/ZnS, and ZnSe: Cu,D/ZnS QD Synthesis

The synthesis of ZnSe, ZnSe:Cu, and ZnSe:Cu,D used herein was an adaptation from Gul et al. (See Gul, S.; Cooper, J. K.; Glans, P.-A.; Guo, J.; Yachandra, V. K.; Yano, J.; Zhang, J. Z. Effect of Al3+ co-doping on the dopant local structure, optical properties, and exciton dynamics in Cu+-doped ZnSe nanocrystals. *ACS Nano* 2013, 7, 8680-8692.). Specifics may be found in the Supplementary Methods provided below along with a description of the ZnS shell addition.

Capping Ligand Synthesis

The capping ligand was synthesized fresh alongside each QD synthesis. In a $N_2$ glove box, a solution was prepared containing 0.1469 g lipoic acid, 0.2639 g trioctylphosphine (TOP), and 0.1907 g oleylamine. The mixture was placed in a 25 mL three neck round bottom flask connected to a Schlenk line and degassed for 10 minutes with 3 pump/purge cycles with dry $N_2$. While stirring, the reaction was heated to 120° C. and maintained for the totality of the QD synthesis (~16 hours). During the reaction between lipoic acid and oleylamine, $H_2O$ is released which can react with TOP and cause it to become oxidized, thus providing electrons to cleave the disulfide bond. Indeed, the reaction color changed from yellow to clear, indicating bond cleavage. The resultant reaction mixture was added directly to the crude ZnSe:Cu,D/ZnS pot where the thiol termination of the ligand engages a strong bidentate interaction with the QD surface at both Zn and S sites.

HRTEM STEM-EELS

TEM investigation was carried out using an FEI F20 UT Tecnai HRTEM/STEM microscope operated at 200 kV accelerating voltage, located at the National Center for Electron Microscopy (NCEM) at Lawrence Berkeley National Laboratory. This microscope is equipped with a post-column energy filter (GIF Tridiem from Gatan) and an EELS detector for analytical characterization.

Steady State Spectroscopic Characterization

The room temperature optical absorption spectrum of the QDs dispersed in DCM was recorded with a Hewlett Packard 8452A diode array spectrometer. The room temperature photoluminescence (PL) spectrum was recorded using a Perkin-Elmer Luminescence spectrometer. Temperature dependent PL measurements were collected on a custom built system at 20-330 K through control by a closed cycle liquid helium cryostat (Janus Research Company, Wilmington, Mass., USA). The sample was excited with a 405 nm continuous wave laser (100 mW Excelsior, Spectra-Physics, Santa Clara, Calif., USA) after passing the laser through a 405 nm notch filter and attenuated to 14 µW and the spot size at the sample was 0.3 mm diameter. The sample luminescence was collected at 90° with respect to the excitation and was filtered through a 407 nm longpass filter and was incident on an Andor Shamrock spectrometer equipped with a 600 lines/mm grating blazed at 500 nm (Andor Technology Ltd., Belfast, UK). The light was recorded with an Andor iDus 410 CCD operated at −90° C. Wavelength calibration was done with a Hg calibration lamp and the CCD and grating efficiency was corrected for using a NIST tracable quartz tungsten halogen 45 W light source with known color temperature.

Time-Resolved Photoluminescence

Time-resolved PL was measured with time-correlated single photon counting (TCSPC) at room temperature using a system and techniques described elsewhere.[29,59] Briefly, a 200 MHz Ti:sapphire laser (tunable 790-820 nm) with an output of 350 mW, was passed through a Conoptics pulse picker to select a 500 KHz pulse train and a BiBO crystal to generate the second harmonic. This ~405 nm centered, 4 µJ, laser was used to excite the sample. The fluorescence light from the sample was collected tangentially to the excitation laser and passed through a monochromator with 0.25 nm resolution. Detection was achieved with an ID100 avalanche photodiode (IDQ, Switzerland). The instrument response function was determined to be 50 ps, as determined from scattering of the excitation light from a non-dairy creamer solution. Data was analyzed with IGOR Pro (wavemetrics) as well as singular value decomposition global fitting procedures developed in-house for Matlab.

DFT Calculations

Calculations on ZnSe, ZnSe:Cu, ZnSe:Cu,Al, ZnSe:Cu,Ga, and ZnSe:Cu,In were performed with the PWscf package contained in the Quantum ESPRESSO code (See Giannozzi, P., et al. QUANTUM ESPRESSO: a modular and open-source software project for quantum simulations of materials. *J. Phys.: Condens. Matter* 2009, 21, 395502).

Density function theory (DFT) calculations were performed with the PBE functional and ultra-soft pseudopotentials on a super cell containing 64 atoms for ZnSe, ZnSe:Cu,Al, ZnSe:Cu,Ga, and ZnSe:Cu,In and 63 atoms for ZnSe:Cu. The optimized unit cell parameter (a) was 5.74 Å. For ionic position optimization, damp dynamics were used with a 4×4×4 K point mesh. The Cu—Se bond distances were constrained to the experimentally determined bond distances from EXAFS, as PBE was not able to duplicate the experimental lattice position of Cu, while the remaining atoms were allowed to vary. SCF and NSCF calculations were performed with kinetic energy cutoff of 70 Ry for wavefunctions and 700 Ry for the charge density, a 8×8×8 K point mesh, and tetrahedral occupations. The local density of states (LDOS) were calculated with projwfc.x packaged with Quantum Espresso.

EXAFS

X-ray absorption measurements at the Cu, Zn and In K-edges were performed at the Stanford Synchrotron Radiation Lightsource (SSRL), on beamline 7-3 at 10 K. The monochromatized radiation from a Si (220) double crystal monochromator was detuned to 50% of its maximum at the metal K-edge to minimize the effects of higher harmonics. The beam size on the sample was reduced to 0.5 mm vertical and 1.0 mm horizontal FWHM. In case of In K-edge, intensity of the incident x-rays ($I_0$) was monitored by Ar filled ion chamber in front of the sample, whereas $N_2$ was used for other measurements. Along with the samples, respective metal foils were measured during each scan using a reference ion chamber to calibrate the energy scale. Zn data was collected in transmission mode, while Cu and In measurements were carried out in fluorescence mode using a 30 element Ge detector (Canberra). QD samples were deposited in plexiglass sample holders with kapton film windows. All data were processed using standard programs based on IFEFFIT (See. Newville, M. IFEFFIT: interactive XAFS analysis and FEFF fitting. *Journal of synchrotron radiation* 2001, 8, 322-324; and Ravel, B.; Newville, M. ATHENA, ARTEMIS, HEPHAESTUS: data analysis for X-ray absorption spectroscopy using IFEFFIT. *Journal of synchrotron radiation* 2005, 12, 537-541).

After calibrating the energy, individual scans were averaged together to improve the signal to noise ratio. Athena software was used for background removal and extraction of EXAFS oscillations $\chi(k)$ as a function of photoelectron wavenumber k. The extracted k-space data, $k^3\chi(k)$, was then used to FT the data into r-space. Theoretical EXAFS models were calculated using FEFF6 (See Zabinsky, S. et al., Multiple-scattering calculations of x-ray-absorption spectra. *Physical Review B* 1995, 52, 2995-3009), and fitting program Artemis was used for fitting the data.

Supplementary Methods

ZnSe/ZnS, ZnSe:Cu/ZnS, and ZnSe: Cu,D/ZnS QD Synthesis

The synthesis of ZnSe, ZnSe:Cu, and ZnSe:Cu,D cores, where D represents $Al^{3+}$, $Ga^{3+}$ or $In^{3+}$, described herein is an adaptation from Gul et al. (See Gul, S., et al. Effect of $Al^{3+}$ co-doping on the dopant local structure, optical properties, and exciton dynamics in $Cu^+$-doped ZnSe nanocrystals. *ACS Nano* 2013, 7, 8680-8692). Selenium powder (<325 mesh, 99.7%) was purchased from Acros Organics. Octadecylamine (ODA), diphenylphosphine (DPP), octadecene (ODE), trioctylphosphine (TOP), trioctylphosphine oxide (TOPO), zinc stearate ($Zn(St)_2$), zinc acetate ($Zn(ac)_2$), aluminum stearate ($Al(St)_3$), indium acetate ($In(ac)_3$), gallium acetylacetonate ($Ga(acac)_3$), S powder, methanol (MeOH), isopropyl alcohol (IPA), and dichloromethane (DCM) were purchased from Sigma Aldrich. Anhydrous reagents were used. Lipoic acid (LA) was purchased from Alfa Aesar. Five solutions were prepared in a dry $N_2$ glove box herein referred to as 'A,' '$B_{Cu,D}$', 'C', 'D', and 'main'. (A) contained 0.028 g Se (355 µmol), 0.2 g ODA (740 µmol), and 0.18 g DPP (970 µmol) which was sonicated with mild heating (40° C.) until the Se was dissolved. It should be noted that heating DPP much above 50° C. can be very dangerous and special care should be taken as the vapor will readily permeate under Teflon-lined septa and dissolve rubber caps. (B) Cu,Al contained 0.01041 g Cu(ac)$_2$ (57.3 µmol), 0.0504 g Al(St)$_3$ (57.4 µmol), 3.70 g ODE, 0.2 g TOPO, and 0.02 g ODA. TOPO and ODA aided solubility. Solution B$_{Cu,Ga}$ contained 0.01029 g Cu(ac)$_2$ (56.7 µmol), 0.02104 g Ga(acac)$_3$ (57.3 µmol), 3.70 g ODE, 0.22 g TOPO, and 0.20 g ODA. Solution B$_{Cu,In}$ contained 0.01041 g Cu(ac)$_2$ (57.3 µmol), 0.01699 g In(ac)$_3$ (58.2 µmol), 3.70 g ODE, 0.32 g TOPO, and 0.20 g ODA. Solution B$_{Cu}$ contained 0.0106 g Cu(ac)$_2$ (58.4 µmol), 3.70 g ODE, 0.22 g TOPO, and 0.20 g ODA. (C) contained 0.90 g Zn(st)$_2$ (1,400 µmol), 0.20 g ODA (740 µmol), 1.5 g TOP (4,000 µmol), and 7 g ODE. Heating was required to achieve solubility for some B$_{Cu,D}$. (D) contained 0.0343 g S (1,070 µmol), 0.2 g DPP (1,070 µmol), 0.1 g ODA (370 µmol), and 8 g ODE. Solution D was also sonicated and mildly heated with solution A to dissolve the S powder. Because DPP was dispersed in a significant quantity of ODE in D, the dangers seen in A were not observed and heating up to 120° C. was not a problem. Finally, the main pot contained 0.018 g Zn(ac)$_2$ (100 µmol), 7.9 g ODE, and 0.05 g TBP (250 µmol).

In a typical reaction, a Schlenk line with N$_2$ and rough pump with liquid nitrogen (L-N$_2$) trap (40 mtorr minimum) was utilized. A 100 mL three neck round bottom flask, with condenser, thermocouple, and septa was evacuated for 12 hours prior to the reaction. After purging with dry N$_2$, the main solution was added to the round bottom flask. This solution was evacuated for a minimum of 30 minutes, followed by three pump/purge cycles. The solution was heated to 100° C. with two more pump/purge cycles. The main flask was then heated to 300° C. upon which solution A was injected rapidly with very fast stirring and an instant color change from colorless to pale yellow was observed. Heating between 280 and 300° C. was maintained for 60 seconds upon which the temperature was rapidly quenched with forced air to 180° C. Note that the solution may become turbid at this point. This temperature was allowed to stabilize prior to the dropwise addition (1 drop per 30-60 sec.) of 175 µL B$_{Cu,D}$. After 10 minutes, the mixture was heated to 240° C. and maintained for 1-3 hours.

A ZnSe over layer on the resultant surface-doped ZnSe QDs was done at the same temperature by adding 250 µL of C. Solution C was maintained independently at ~100-120° C. under N$_2$ to keep the solution dissolved. During the addition, the injection needle was also heated with a heat gun toward the reaction flask to keep the solution dissolved. The 250 µL of C was added dropwise over the curse of 60 sec while maintaining vigorous stirring. This was allowed to react for 1 hour whereupon an additional 250 µL was added. In 30-minute intervals, solution C was added in 250 µL volumes until the main pot became clear yellow which was related to excess Zn in solution from the total Zn added. An additional 1 mL of C was added at this point to drive the Zn concentration up in the main pot.

A ZnS shell layer was added on top of the resultant ZnSe:Cu/ZnSe QDs through the cycled addition of D and C over the course of 2 hours at a temperature maintained between 220-240° C. A typical addition was 1-2 mL of D after which 15 minutes were allowed to pass after which 1-2 mL of C were added and cooked for 15 minutes. The addition of both D and C should be done dropwise to keep from nucleating new particles. After finishing the addition of D and C, there may be ~1-2 mL of D left over but the main pot should be clear. The mixture was maintained at 240° C. for 30 minutes. The temperature was dropped to 220° C. and the capping ligand mixture was then added dropwise. The undoped ZnSe QDs were prepared in the same fashion as described above except there was no addition of B. Otherwise, all steps were identical. After the addition of the capping ligand, the reaction was cooled slowly to room temperature.

The crude reaction mixture was cleaned with liquid/liquid extraction with a mixture of MeOH and DCM. The extraction was achieved by adding the main pot mixture to a 250 mL separatory funnel and then adding a volume of MeOH (~50-100 mL). The main pot mixture was denser than the MeOH layer, so DCM was added until an inversion was achieved (~10 mL). Addition of DCM is beneficial as it improves the separation. The MeOH/DCM layer was discarded. This process was continued until the MeOH/DCM layer was no longer turbid. A gradual increase in the MeOH/DCM ratio toward the end improved the removal of ODE. When the final ODE/QD layer was lowered to ~1-2 mL, a final rinse was done by floating the NC layer on the MeOH/ODE and adding a small amount of IPA. The resulting crystals solidified and were collected by centrifuge. The QDs were finally dried under a stream of argon and stored.

Extended X-Ray Absorption Fine Structure Fitting

For EXAFS curve fitting, the ab initio amplitudes and phases calculated using FEFF 6, were used in the EXAFS equation:

$$\chi(k) = S_0^2 \sum_j \frac{N_j}{kR_j^2} f_{\text{eff}j}(\pi, k, R_j) e^{-2\sigma_j^2 k^2} e^{-2R_j/\lambda_j(k)} \sin(2kR_j + \phi_{ij}(k)) \quad (4)$$

$f_{\text{eff}j}(\pi,k, R_j)$ denotes the ab initio amplitude function for shell j with the coordination number N$_j$, and the Debye-Waller term $e^{-2\sigma_j^2 k^2}$ determines the amplitude damping due to thermal and static disorder in absorber-backscatterer distances. The losses due to inelastic scattering are reflected by mean free path term $e^{-2R_j/\lambda_j(k)}$, where $\lambda_j(k)$ represents the electron mean free path. The EXAFS oscillations are reflected in the sinusoidal term, $\sin(2kR_j+\phi_{ij}(k))$ where $\phi_{ij}(k)$ is the ab initio phase function for shell j. $S_0^2$ represents the amplitude reduction factor due to shake-up/shake-off processes at the absorbing atom(s). In theoretical EXAFS signal, variable parameters included the passive electron reduction factor ($S_0^2$), the bond distance between the absorbing atom and its nearest neighbors (R$_j$), mean square displacement of the bond distance ($\sigma_j^2$), and the co-ordination number (N$_j$) of the nearest neighbors around the central atom. In case of each element, the value for ($S_0^2$) was determined from the fits to the respective reference metal foils' data, and was fixed during the fits. Other parameters (N, R, $\sigma^2$) were allowed to vary and fine-tuned during the fitting process. Fit parameters corresponding to the best fit results have been reported in Table 2 herein.

Supplementary Discussion

Gaussian Fitting of PL Spectra

Prior to fitting the PL spectra, the intensity vs. wavelength spectra were transformed to photon flux vs. photon energy by Equation 5 where $I_0(\lambda)$ is the intensity measured in units of wavelength:

$$I_0(\lambda)d\lambda = I_0[\lambda(E)]dE\frac{d\lambda}{dE} = I_0[\lambda(E)]\frac{\lambda^2}{hc}(-dE) = \frac{\lambda^2 I_0}{1240 \text{ ev nm}}dE \quad (5)$$

The resulting fits of the PL spectra and tabulated values for the Gaussian peaks for each sample are shown in FIG.

14. The blue emitting ZnSe/ZnS QDs have a prominent emission centered at 437 nm with some asymmetric tailing into the red. Gaussian fitting of this feature resulted in three peaks at 435 nm (2.851 eV), 448 nm (2.769 eV), and 461 nm (2.689 eV), with full-width at half max (FWHM) of 0.12, 0.12, and 0.20 eV, respectively. The 434 nm emission, related to the excitonic emission, is higher in energy than the bulk bandgap (2.70 eV) as a result of quantum confinement. Compared to the bandgap measured based on absorption edge (2.97 eV), the exciton binding energy in these QDs is approximately 110 meV, which is consistent with that predicted for ZnSe/ZnS (See Gul, S., et al. Effect of $Al^{3+}$ co-doping on the dopant local structure, optical properties, and exciton dynamics in $Cu^+$-doped ZnSe nanocrystals. *ACS Nano* 2013, 7, 8680-8692). The quantum confinement observed is consistent with the size of the ZnSe core as measured by TEM (~8 nm diameter), and the reported Bohr exciton radius of bulk ZnSe (4.5 nm) (See Ramanathan, S., et al. Fluorescence spectroscopy of electrochemically self-assembled ZnSe and Mn:ZnSe nanowires. *Nanotechnology* 2008, 19, 195601).

With the incorporation of $Cu^+$ into the ZnSe/ZnS host, a new emission peak in the green was observed, with a peak at 513 nm, along with some host-related emission (436 nm). A multi Gaussian fit to the PL spectrum resulted in four bands centered at 437 nm (2.837 eV), 453 nm (2.738 eV), 517 nm (2.398 eV), and 583 nm (2.127 eV), with FWHM of 0.11, 0.12, 0.34, and 0.16 eV, respectively. The 514 nm emission is attributed to $Cu^+$ that acts to trap the photogenerated hole from the VBM creating an intermediate $Cu^{2+}$. The photogenerated electron can decay via two major pathways, either to a hole in the VBM, resulting in 436 nm emission, or to annihilate the $Cu^{2+}$ photohole, giving the 514 nm emission. The difference in energy between the bandgap and the Cu emission results in a Cu acceptor state located at VBM+0.56 eV. The additional peak at 580 nm, which accounts for the red tailing of the Cu emission, is attributed to DAP recombination between the photogenerated $Cu^{2+}$ and a donor state at the CBM−0.27 eV. As Cu dopes the ZnSe lattice as a +1 ion (as determined by X-ray absorption near edge structure (XANES)$^1$) at a $Zn^{2+}$ site, charge balancing the lattice requires a second $Cu^+$ to dope near the first and a $V_{Se}^{2-}$ to be created. This results in a neutral charge in the QD, however, the $V_{Se}^{2-}$ introduces a dangling bond defect within the QD and next to the Cu center. In conjunction with a previous report on ZnSe:Cu (See Gul, S., et al. Effect of $Al^{3+}$ co-doping on the dopant local structure, optical properties, and exciton dynamics in $Cu^+$-doped ZnSe nanocrystals. *ACS Nano* 2013, 7, 8680-8692.), this $V_{Se}^{2-}$-related state is associated with DAP recombination at 580 nm emission.

Similar to ZnSe:Cu/ZnS, introducing $Al^{3+}$ as a codopant with Cu in ZnSe resulted in a green emission band centered at 509 nm but with increased host emission at 432 nm. Analysis by Gaussian fitting resolved peaks at 432 nm (2.869 eV), 447 nm (2.771 eV), and 511 nm (2.42 eV), with FWHM of 0.12, 0.12, and 0.35 eV, respectively. Similar to the singly-doped sample, the 509 nm emission is attributed to the $CBM^-\rightarrow Cu^{2+}$ transition. This places the $Cu^+$ state at VBM+0.54 eV. The relatively blue shifted Cu emission here compared to the singly-doped sample is indicative of a slight change in the Cu local structure, as seen in the EXAFS spectra. The significant amount of bandgap emission in this sample suggests that the donor state introduced by $Al^{3+}$ is at or near the CBM because photoelectron trapping at a donor state was not seen in this system. Contrary to a previous report of ZnSe:Cu,Al (See Gul, S., et al. Effect of $Al^{3+}$ co-doping on the dopant local structure, optical properties, and exciton dynamics in $Cu^+$-doped ZnSe nanocrystals. *ACS Nano* 2013, 7, 8680-8692), the significant amount of host emission in this system is attributed to improved surface passivation and consequently decreased photoelectron trapping at surface dangling bonds resulting in non-radiative decay.

With $Ga^{3+}$ codoping, the PL was shifted significantly to the red compared to the previously discussed samples, resulting in very clean yellow emission by eye. The host emission seen in the previous samples was also completely eliminated. Two Gaussian peaks were required to fit the PL spectrum at 548 nm (2.263 eV) and 609 nm (2.037 eV), with FWHM of 0.36 and 0.32 eV, respectively. Taking the energy level of the $Cu^+$ acceptor state to be unaffected by the addition of $Ga^{3+}$, at least to a first approximation, the red shift of the PL can be attributed to a donor state from $Ga^{3+}$ located at CBM−0.15 eV. The primary emission observed at 542 nm is therefore due to DAP recombination between the photogenerated species: $Ga^{+2}\rightarrow Cu^{+2}$. Effective localization of the photoelectron into the $Ga^{+3}$ donor state is responsible for the elimination of the host emission in this sample. The red tailing represented by the second peak at 609 nm can be assigned to $Ga^{3+}$-related emission due to Ga:ZnSe which has been reported to have bulk emission centered around 600 nm (See Pawlikowski, J. M. Absorptivity and photoluminescence of compensated ZnSe:Ga. *Solid State Commun.* 1985, 55, 31-33).

Finally, In co-doping with Cu exhibits the largest red shift of all the samples studied and appeared orange by eye under UV illumination. Again, the PL spectrum shows no evidence of host-related emission. Fitting of the PL spectrum required two Gaussian peaks at 571 nm (2.171 eV) and 624 nm (1.988 eV), with FWHM of 0.33 and 0.26 eV, respectively. The donor state related to In, again assuming that the Cu state is constant at VBM+0.56 eV, is at CBM−0.24 eV. Similar to the Ga codoped sample, trapping of the photoelectron at the In donor is responsible for the lack of host emission seen.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A core/shell nanocrystal, comprising:
   a core;
   (i) a shell formed on a surface of the core, wherein the core/shell nanocrystal is co-doped with a metal dopant and at least one Group 13 trivalent cation, and wherein the metal dopant is $Cu^+$, or (ii) an undoped shell formed on a surface of the core, wherein the core of the core/shell nanocrystal is co-doped with a metal dopant and at least one Group 13 trivalent cation, wherein the metal dopant is $Cu^+$, and an undoped passivation shell formed on a surface of the undoped shell, or (iii) an undoped shell formed on a surface of the core, wherein the core of the core/shell nanocrystal is co-doped with a metal dopant and at least one Group 13 trivalent cation, wherein the metal dopant is $Cu^+$; and
   a capping ligand, wherein the capping ligand has the structure:

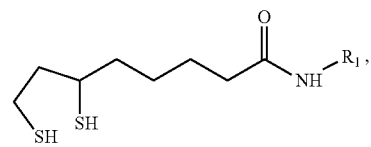

wherein $R_1$ is $—CH_2(CH_2)_7CH=CH(CH_2)_7CH_3$ or $—CH_2(CH_2)_6CH_3$; and
   wherein the capping ligand is attached to a surface of the shell in (i), or
   wherein the capping ligand is attached to a surface of the undoped passivation shell in (ii), or
   wherein the capping ligand is attached to a surface of the undoped shell in (iii).

2. The core/shell nanocrystal of claim 1, wherein the metal dopant and the at least one Group 13 trivalent cation are present in the core in (i), the shell in (i), or both.

3. The core/shell nanocrystal of claim 1, wherein the core is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; and the shell in (i) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; or the undoped shell in (ii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; or the undoped shell in (iii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof.

4. The core/shell nanocrystal of claim 1, wherein the core is comprised of ZnSe; and the shell in (i) is comprised of ZnS, or the undoped shell in (ii) is comprised of ZnS, or the undoped shell in (iii) is comprised in ZnS.

5. The core/shell nanocrystal of claim 1, wherein the at least one Group 13 trivalent cation is selected from $Al^{3+}$, $Ga^{3+}$, $In^{3+}$, and any combinations thereof.

6. The core/shell nanocrystal of claim 1, wherein the core/shell nanocrystal comprises an undoped shell formed on a surface of the core, wherein the core of the core/shell nanocrystal is co-doped with a metal dopant and at least one Group 13 trivalent cation, and wherein the metal dopant is $Cu^+$, and an undoped passivation shell formed on a surface of the undoped shell, wherein the capping ligand is attached to the undoped passivation shell.

7. The core/shell nanocrystal of claim 1, wherein $R_1$ is —$CH_2(CH_2)_7CH$=$CH(CH_2)_7CH_3$.

8. The core/shell nanocrystal of claim 1, wherein the core/shell nanocrystal is a quantum dot.

9. The core/shell nanocrystal of claim 1, wherein the core/shell nanocrystal comprises an undoped shell formed on a surface of the core, wherein the core of the core/shell nanocrystal is co-doped with a metal dopant and at least one Group 13 trivalent cation, wherein the metal dopant is $Cu^+$, and wherein the capping ligand is attached to a surface of the undoped shell.

10. The core/shell nanocrystal of claim 1, wherein $R_1$ is —$CH_2(CH_2)_6CH_3$.

11. The core/shell nanocrystal of claim 1, wherein the undoped passivation shell in (ii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof.

12. The core/shell nanocrystal of claim 1, wherein the undoped passivation shell in (ii) is comprised of ZnS.

13. A method of making a core/shell nanocrystal, the method comprising:
    forming a core;
    (i) forming a shell on a surface of the core so as to make the core/shell nanocrystal, wherein the core/shell nanocrystal is co-doped with a metal dopant and at least one Group 13 trivalent cation, and wherein the metal dopant is $Cu^+$, or (ii) forming an undoped shell on a surface of the core so as to make the core/shell nanocrystal, wherein the core of the core/shell nanocrystal is co-doped with a metal dopant and at least one Group 13 trivalent cation, and wherein the metal dopant is $Cu^+$, and forming an undoped passivation shell on a surface of the undoped shell, or (iii) forming an undoped shell on a surface of the core so as to make the core/shell nanocrystal, wherein the core of the core/shell nanocrystal is co-doped with a metal dopant and at least one Group 13 trivalent cation, and wherein the metal dopant is $Cu^+$;
    providing a capping ligand, wherein the capping ligand has the structure:

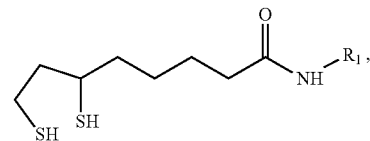

wherein $R_1$ is —$CH_2(CH_2)_7CH$=$CH(CH_2)_7CH_3$ or —$CH_2(CH_2)_6CH_3$; and attaching the capping ligand to a surface of the shell in (i), or attaching the capping ligand to a surface of the undoped passivation shell in (ii), or attaching the capping ligand to a surface of the undoped shell in (iii).

14. The method of claim 13, wherein the metal dopant and the at least one Group 13 trivalent cation are present in the core in (i), the shell in (i), or both.

15. The method of claim 13, wherein the core is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; and the shell in (i) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; or the undoped shell in (ii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof; or the undoped shell in (iii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof.

16. The method of claim 13, wherein the core is comprised of ZnSe; and the shell in (i) is comprised of ZnS, or the undoped shell in (ii) is comprised of ZnS, or the undoped shell in (iii) is comprised of ZnS.

17. The method of claim 13, wherein the at least one Group 13 trivalent cation is selected from $Al^{3+}$, $Ga^{3+}$, $In^{3+}$, and any combinations thereof.

18. The method of claim 13, wherein the method comprises forming the undoped shell on a surface of the core so as to make the core/shell nanocrystal, wherein the core of the core/shell nanocrystal is co-doped with a metal dopant and at least one Group 13 trivalent cation, and wherein the metal dopant is $Cu^+$, forming an undoped passivation shell on a surface of the undoped shell, and attaching the capping ligand to the undoped passivation shell.

19. The method of claim 13, wherein $R_1$ is —$CH_2(CH_2)_7CH$=$CH(CH_2)_7CH_3$.

20. The method of claim 13, wherein the core/shell nanocrystal is a quantum dot.

21. The method of claim 13, wherein the method comprises forming the undoped shell on a surface of the core so as to make the core/shell nanocrystal, wherein the core of the core/shell nanocrystal is co-doped with a metal dopant and at least one Group 13 trivalent cation, and wherein the metal dopant is $Cu^+$, and attaching the capping ligand to a surface of the undoped shell.

22. The method of claim 13, wherein $R_1$ is —$CH_2(CH_2)_6$$CH_3$.

23. The method of claim 13, wherein the undoped passivation shell in (ii) is comprised of ZnSe, ZnS, ZnTe, CdS, CdSe, CdTe, HgS, HgSe, HgTe, PbS, PbSe, PbTe, AlN, AlP, AlAs, GaN, GaP, GaAs, InN, InP, or InAs, and any mixtures thereof.

24. The method of claim 13, wherein the undoped passivation shell in (ii) is comprised of ZnS.

* * * * *